United States Patent
Li et al.

(10) Patent No.: US 10,429,477 B2
(45) Date of Patent: *Oct. 1, 2019

(54) SYSTEM AND METHOD FOR FLIP ANGLE DETERMINATION IN MAGNETIC RESONANCE IMAGING

(71) Applicant: SHANGHAI UNITED IMAGING HEALTHCARE CO., LTD., Shanghai (CN)

(72) Inventors: Guobin Li, Shanghai (CN); Chaohong Wang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 252 days.

This patent is subject to a terminal disclaimer.

(21) Appl. No.: 15/321,992

(22) PCT Filed: Aug. 21, 2015

(86) PCT No.: PCT/CN2015/087818
§ 371 (c)(1),
(2) Date: Dec. 23, 2016

(87) PCT Pub. No.: WO2017/031638
PCT Pub. Date: Mar. 2, 2017

(65) Prior Publication Data
US 2017/0212197 A1 Jul. 27, 2017

(51) Int. Cl.
*G01R 33/561* (2006.01)
*A61B 5/00* (2006.01)
(Continued)

(52) U.S. Cl.
CPC .......... *G01R 33/5617* (2013.01); *A61B 5/055* (2013.01); *G01R 33/4808* (2013.01);
(Continued)

(58) Field of Classification Search
CPC . A61B 5/055; A61B 2576/026; A61B 5/0042; A61B 5/4244; A61B 5/4519; A61B 5/4528; A61B 5/4566; A61B 5/4571; A61B 5/4585; A61B 5/7257; G01R 33/288; G01R 33/4808; G01R 33/543; G01R 33/5615; G01R 33/5617
See application file for complete search history.

(56) References Cited

U.S. PATENT DOCUMENTS 5,245,282 A   9/1993  Mugler, III et al.
6,272,369 B1  8/2001  Tan
(Continued)

OTHER PUBLICATIONS

International Search Report for PCT/CN2015/087818 dated May 20, 2016, 4 pages.
(Continued)

*Primary Examiner* — Rishi R Patel
(74) *Attorney, Agent, or Firm* — Metis IP LLC

(57) ABSTRACT

A system and method for calculating a flip angle schedule is provided. The technique includes selecting an initial condition, providing a function for calculating flip angles, calculating flip angles, assessing the flip angles, and repeating the calculation of the flip angles by adjusting the function until a desired flip angle schedule is obtained.

19 Claims, 15 Drawing Sheets

(51) Int. Cl.
G01R 33/48 (2006.01)
A61B 5/055 (2006.01)
G01R 33/54 (2006.01)
G01R 33/28 (2006.01)

(52) U.S. Cl.
CPC ....... *G01R 33/543* (2013.01); *G01R 33/5615* (2013.01); *A61B 5/0042* (2013.01); *A61B 5/425* (2013.01); *A61B 5/4244* (2013.01); *A61B 5/4519* (2013.01); *A61B 5/4528* (2013.01); *A61B 5/4566* (2013.01); *A61B 5/4571* (2013.01); *A61B 5/4585* (2013.01); *A61B 5/7257* (2013.01); *A61B 2576/026* (2013.01); *G01R 33/288* (2013.01)

(56) References Cited

U.S. PATENT DOCUMENTS

| | | |
|---|---|---|
| 6,603,989 B1 | 8/2003 | Yablonskiy |
| 7,164,268 B2 | 1/2007 | Mugler, III et al. |
| 7,705,597 B2 | 4/2010 | Horger et al. |
| 8,228,060 B2 | 7/2012 | Busse |
| 2004/0051527 A1 | 3/2004 | Mugler, III et al. |
| 2007/0249929 A1 | 10/2007 | Jeong et al. |
| 2008/0319301 A1 | 12/2008 | Busse |
| 2009/0009168 A1 | 1/2009 | Witschey et al. |
| 2009/0033328 A1 | 2/2009 | Feiweier |
| 2013/0271132 A1 | 10/2013 | Griswold |
| 2013/0342202 A1 | 12/2013 | Mugler, III et al. |
| 2014/0077805 A1* | 3/2014 | Hoshino ............ G01R 33/5617 324/307 |
| 2014/0084918 A1 | 3/2014 | Kurokawa |
| 2017/0184694 A1 | 6/2017 | Li et al. |
| 2017/0212197 A1 | 7/2017 | Li et al. |

OTHER PUBLICATIONS

M. Weigel, et al. "Extended phase graphs with anisotropic diffusion." JMR 205:276-285 (2010).

Juergen Hennig, et al. "Calculation of Flip Angles for Echo Trains With Predefined Amplitudes With the Extended Phase Graph (EPG)-Algorithm: Principles and Applications to Hyperecho and TRAPS Sequences" Mag. Reson 51:68-80 (2004).

J. P. Mugler, et al. "Practical Implementation of Optimized Tissue-Specific Prescribed Signal Evolutions for Improved Turbo-Spin-Echo Imaging." Mag. Reson 11:203 (2003).

JP Mugler, et al. "Three-Dimensional T2-Weighted Imaging of the Brain Using Very Long Spin-Echo Trains." Proceedings of the 8th Annual Meeting of ISMRM at 687 (2000).

J. Hennig, et al. "RARE Imaging: A Fast Imaging Method for Clinical MR." Mag. Reson 3:823-833 (1986).

A. J. Madhuranthakam, et al. "Sensitivity of Low Flip Angle SSFSE of the Abdomen to Cardiac Motion." Mag. Reson, 15 at 2523 (2007).

Reed F. Busse, et al. "Effects of Refocusing Flip Angle Modulation and View Ordering in 3D Fast Spin Echo." Mag. Reson, 60:640-649 (2008).

Andreas M. Loening et al., Increased speed and image quality in single-shot fast spin echo imaging via variable refocusing flip angles, Journal of Magnetic Resonance Imaging 6(42), 2015, pp. 1747-1758.

Juergen Hennig et al., "Calculation of flip angles for echo trains with predefined amplitudes with the extended phase graph(EPG)-algorithm: Principles and applications to hyperecho and TRAPS sequences", Magnetic Resonance in Medicine, 1(51), 2003, pp. 68-80.

European Search Report in European Application No. 15896596.2 dated Jul. 9, 2018, 15 pages.

* cited by examiner

SYSTEM AND METHOD FOR FLIP ANGLE DETERMINATION IN MAGNETIC RESONANCE IMAGING

CROSS-REFERENCE TO RELATED APPLICATIONS

This application is a U.S. national stage under 35 U.S.C. § 371 of International Application No. PCT/CN2015/087818, filed on Aug. 21, 2015, designating the United States of America, the entire contents of which are hereby incorporated by reference.

TECHNICAL FIELD

The present disclosure generally relates to magnetic resonance imaging (MRI), and more particularly, to a system and method for determining a flip angle schedule for an echo train pulse sequence applicable in magnetic resonance imaging.

BACKGROUND

Magnetic resonance imaging (MRI) systems may be used to diagnose and treat medical conditions by exploiting a powerful magnetic field and radio frequency (RF) techniques. When a subject of interest is exposed in a magnetic field, main field B0, individual nucleus spins in the subject tend to align with field B0, but still precess at the Larmor frequency. The subject may include any substance, tissue, organ, an object or body of interest, or the like, or any combination thereof. The overall motion of the nucleus spins in the subject may be simplified as net magnetization (M) which is the averaged sum of many individual nucleus spins. A second magnetic field, a radio frequency field (field B1), is applied to M, causing M to precess away from field B0. An induced current is generated due to the sweep of M past the RF coils in an MRI system. The induced current may be termed as a magnetic resonance (MR) signal. During imaging, the MR signals are given different phase encoding and different frequency encoding, according to the gradient magnetic field. The image may thus be reconstructed by two-dimensional or three-dimensional Fourier Transform.

The spin echo is an effect utilized to generate a series of echoes when an excitation RF pulse and a certain number of refocusing RF pulses are applied. A group of generated echoes are called an echo train. The number of echoes obtained in an echo train is called echo train length (ETL). A typical echo train is generated by the application of a 90° excitation RF pulse and a series of 180° refocusing RF pulses. However, due to the power deposition or specific absorption rate (SAR) caused by high frequency RF pulses, the temperature of the object or body (e.g., a tissue) may rise to a certain degree that may cause a tissue damage, and/or the reconstructed image may be blurry or have other artifacts. The application of variable flip angles may reduce power deposition, and may decrease the image acquisition time. The term "flip angle" may refer to the rotation of the net magnetization vector M by a radio frequency pulse relative to the main magnetic field B0. Thus, it would be desirable to develop a system and method for determining, improving, or optimizing a flip angle schedule applicable in MRI.

SUMMARY OF THE INVENTION

In a first aspect of the present disclosure, a magnetic resonance imaging (MRI) system is provided. In some embodiments, the MRI system may include an MRI scanner, a control unit, and a processing unit. The processing unit may be configured or used to select or set an initial condition relating to a first phase of an echo train. The initial condition may include initial values of a first flip angle, a second flip angle, and a first characteristic parameter. A first function corresponding to the first phase of the echo train may be provided. The first function may relate to, e.g., the first flip angle, the second flip angle, and/or the first characteristic parameter. One or more flip angles corresponding to one or more spin echoes of the first phase may be calculated based on the first function. The one or more flip angles may be assessed according to a first criterion. If the first criterion is not satisfied, the processing unit may revise the first function by adjusting, e.g., at least one of the first flip angle, the second flip angle, or the first characteristic parameter, and repeat calculating one or more flip angles and assessing the one or more flip angles. The first function may provide a flip angle schedule corresponding to the first phase of the echo train for magnetic resonance imaging. The control unit may be configured or used to control the MRI scanner according to the flip angle schedule.

In a second aspect of the present disclosure, a method is provided. The method may include one or more of the following operations. An initial condition relating to a first phase of an echo train may be selected or set. The initial condition relating to a first phase of an echo train may include initial values of a first flip angle, a second flip angle, and a first characteristic parameter may be selected. A first function corresponding to the first phase of the echo train may be provided. The first function may relate to, e.g., the first flip angle, the second flip angle, and the first characteristic parameter. One or more flip angles corresponding to one or more spin echoes of the first phase may be calculated based on the first function. The one or more flip angles may be assessed according to a first criterion. If the first criterion is not satisfied, the first function may be revised by adjusting at least one of the first flip angle, the second flip angle, or the first characteristic parameter, and one or more flip angles may be calculated and assessed repeatedly. The first function may provide a flip angle schedule corresponding to the first phase of the echo train for magnetic resonance imaging.

In some embodiments, the first function may include a function of the spin echo number.

In some embodiments, the first function may include the Bloch equation, the extended phase graph (EPG) algorithm, a polynomial, a linear function, a trigonometric function, an anti-trigonometric function, an exponential function, a power function, a logarithmic function, or the like, or any combination thereof.

In some embodiments, the assessing of the one or more flip angles of the first phase may include calculating a first signal evolution based on the one or more flip angles of the first phase, and evaluating the first signal evolution according to the first criterion. The calculation may include using the Bloch equation or the EPG algorithm. In some embodiments, the first criterion may include a first threshold. The assessing of the one or more flip angles of the first phase may include determining whether a maximum signal in the first signal evolution equals to or exceeds the first threshold.

In some embodiments, a reference signal schedule corresponding to the first phase may be provided. The reference signal schedule may include one or more reference signals corresponding to the one or more echoes of the first phase. The reference signal schedule may correspond to an echo train with an expected signal intensity of every echo. The reference signal schedule may be a loose restriction on the signal intensity of one or more echoes. The reference signal schedule may specify a desired signal intensity, without specifying how or when the corresponding echo (the echo that corresponds to the signal of the specified intensity) occurs in the echo train. The reference signal schedule may include a restriction on the trend of each phase in one or more echo trains. In some embodiments, the reference signal schedule may be relating to T1 or T2 of a tissue to be measured using the flip angle schedule corresponding to the first phase of the echo train for magnetic resonance imaging. In some embodiments, the assessing of the one or more flip angles of the first phase may include calculating a first signal evolution based on the one or more flip angles of the first phase, and comparing the first signal evolution with the reference signal schedule. The first criterion may relate to the difference between the first signal evolution and the reference signal schedule. In some embodiments, the first criterion may include one or more equations for the comparison between the signal evolution and the reference signal schedule. The equation may be based on L1 norm, L2 norm, a standard deviation, or the like, or any combination thereof.

In some embodiments, the number of phase(s) in an echo train and/or the number of echo(s) in each phase may be determined according to the characteristics of reference signal schedule, a certain rule, or randomly.

In some embodiments, the adjusting of the at least one of the first flip angle, the second flip angle, or the first characteristic parameter may include using recursion, a bisection method, an exhaustive search, a greedy algorithm, a divide and conquer algorithm, a dynamic programming method, an iterative method, a branch-and-bound algorithm, a backtracking algorithm, or the like, or any combination thereof.

In some embodiments, an initial condition relating to a second phase of the echo train may be selected or set. The initial condition may include initial values of a third flip angle, a fourth flip angle, and a second characteristic parameter. A second function corresponding to the second phase may be provided. The second function may relate to, e.g., the third flip angle, the fourth flip angle, and/or the second characteristic parameter. One or more flip angles corresponding to one or more spin echoes of the second phase may be calculated based on the second function. The one or more flip angles of the second phase may be assessed according to a second criterion. If the second criterion is not satisfied, the second function may be revised by adjusting, e.g., at least one of the third flip angle, the fourth flip angle, or the second characteristic parameter, and repeat calculating one or more flip angles and assessing the one or more flip angles. The second function may provide a flip angle schedule corresponding to the second phase of the echo train for magnetic resonance imaging. One or more features described in connection with the first phase may be applicable with respect to the determination of the flip angle schedule of the second phase.

In some embodiments, the third flip angle may be same as the initial value of the second flip angle or the adjusted second flip angle.

In some embodiments, the initial condition relating to the first phase or the second phase may include at least one of an echo train duration time, an echo train length, a phase number, a number of the echoes in the first phase, or the like, or any combination thereof. The phase number may be 1, 2, 3, or more.

In some embodiments, the magnetic resonance imaging may include T1 weighted imaging, T2 weighted imaging, proton density weighted imaging, or the like, or any combination thereof.

In some embodiments, an automatic or semi-automatic mode may be provided in performing one or more of the above operations based on, e.g., information (or referred to as preferred information) saved or acquired from historic or prior imaging procedures or set by an external resource.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "unit," "module," and/or "block" used herein are one method to distinguish different components, elements, parts, section or assembly of different level in ascending order. However, the terms may be displaced by other expression if they may achieve the same purpose.

It will be understood that when a unit, module or block is referred to as being "on," "connected to" or "coupled to" another unit, module, or block, it may be directly on, connected or coupled to the other unit, module, or block, or intervening unit, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an" and "the" may be intended to include the plural forms as well, unless the context clearly indicates otherwise. It will be further understood that the terms "include," and/or "comprising," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

Figure 1:
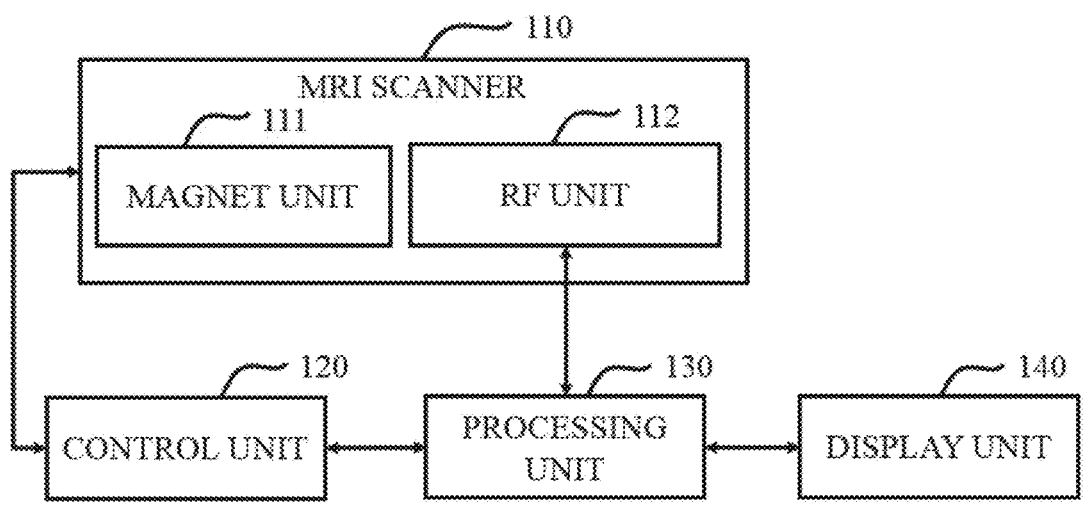
FIG. 1 is a block diagram depicting a magnetic resonance imaging (MRI) system according to some embodiments of the present disclosure.

FIG. 1 is a block diagram of a magnetic resonance imaging system according to some embodiments of the present disclosure. As illustrated, an MRI system 100 may include an MRI scanner 110, a control unit 120, a processing unit 130, and a display unit 140. The MRI scanner 110 may include a magnet unit 111 and a radio frequency (RF) unit 112. The magnet unit 111 may include a main magnet filed generator and/or a gradient magnet field generator (not shown in FIG. 1). The main magnet field generator may be configured or used to create a static magnetic field B0 during an MRI process. The main magnet may be of various types including, for example, a permanent magnet, a superconducting electromagnet, a resistive electromagnet, etc. The gradient magnet field generator may be configured or used to generate magnet field gradients to the main magnet field B0 in the x, y, and/or z directions. The gradient magnet field may be configured or used to encode the spatial information of a subject located in the MRI scanner 110. The RF unit 112 may include RF transmitting coils and/or receiving coils. These RF coils may be configured or used to transmit RF signals to or receive RF signals from a subject of interest. In some embodiments, the function, size, type, geometry, position, amount, and/or magnitude of the magnet unit 111 and/or of the RF unit 112 may be determined or changed according to one or more specific conditions. For example, according to the difference in function and size, the RF coils may be classified as volume coils and local coils. In some embodiments of the present disclosure, the volume coils may include birdcage coils, transverse electromagnetic coils, surface coils, saddle coils, etc. In some embodiments of the present disclosure, the local coils may include birdcage coils, solenoid coils, saddle coils, flexible coils, etc.

The control unit 120 may control the magnet unit 111 and/or the RF unit 112 of the MRI scanner 110, the processing unit 130, and/or the display unit 140. The control unit 120 may receive information from or send information to the MRI scanner 110, the processing 130, and/or the display unit 140. According to some embodiments of the present disclosure, the control unit 120 may receive commands from the display unit 140 provided by, e.g., a user, and adjust the magnet unit 111 and/or RF unit 112 to take images of a subject of interest according to the received commands. The processing unit 130 may be configured or used to process different kinds of information received from different units.

For further understanding the present disclosure, several examples are given below, but the examples do not limit the scope of the present disclosure. For example, in some embodiments, the processing unit 130 may process MR signals received from the RF unit 112 and generate one or more MR images based on these signals and deliver the images to the display unit 140. In some embodiments, the processing unit 130 may process data input by a user or an operator via the display unit 140 and transform the data into specific commands, and supply the commands to the control unit 120. The display unit 140 may be configured or used to receive input and/or display output information. The input and/or output information may include programs, software, algorithms, data, text, number, images, voice, or the like, or any combination thereof. For example, a user or an operator may input some initial parameters or conditions to initiate a scan. As another example, some information may be imported from external resource, such as a floppy disk, a hard disk, a wireless terminal, or the like, or any combination thereof.

It should be noted that the above description of the MRI system 100 is merely provided for the purposes of illustration, and not intended to limit the scope of the present disclosure. For persons having ordinary skills in the art, multiple variations and modifications may be made under the teachings of the present disclosure. For example, the assembly and/or function of the MRI system 100 may be varied or changed according to specific implementation scenarios. Merely by way of example, some other components may be added into the MRI system 100, such as a patient positioning unit, a gradient amplifier unit, and other devices or units. Note that the MRI system may be a traditional or a single-modality medical system, or a multi-modality system including, e.g., a positron emission tomography-magnetic resonance imaging (PET-MU) system, a computed tomography-magnetic resonance imaging (CT-MRI) system, a remote medical MRI system, and others, etc. However, those variations and modifications do not depart from the scope of the present disclosure.

Figure 2:
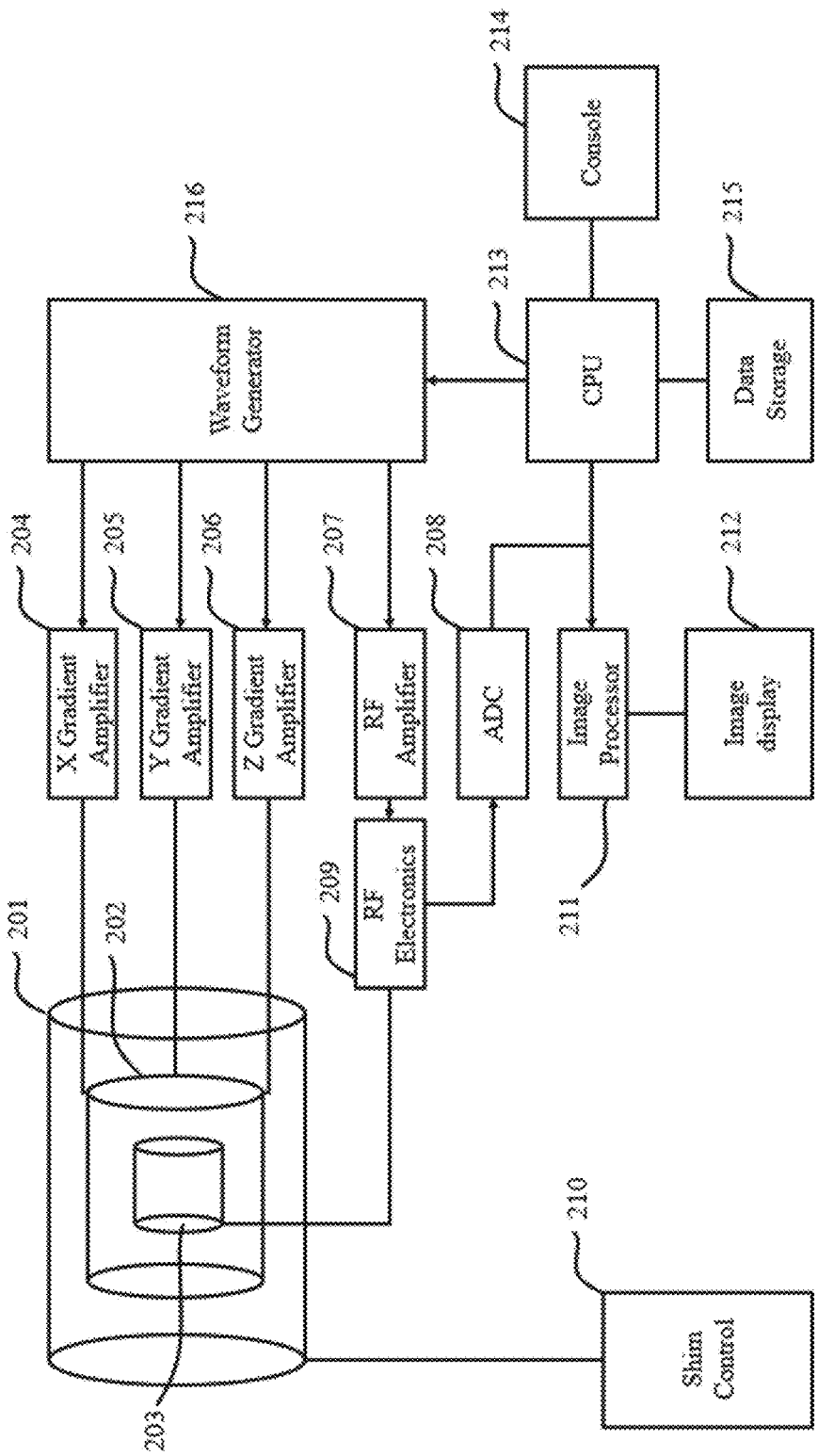
FIG. 2 is a block diagram depicting an MRI system according to some embodiments of the present disclosure.

FIG. 2 is a block diagram of the MRI system 100 according to some embodiments of the present disclosure. As shown in the figure, the main field and shim coils 201 may be configured or used to generate a main magnetic field that may be applied to an object exposed inside the field. The main filed and shim coils 201 may also be configured or used to control the homogeneity of the generated main field. Gradient coils 202 may be located inside the main field and shim coils 201. The gradient coils 202 may generate a second magnetic field or referred to as a gradient field. The gradient coils 202 may distort the main field generated by the main field and shim coils 201 so that the magnetic orientations of the protons of an object may vary as a function of their positions inside the gradient field. The gradient coils 202 may include X coils, Y coils, and/or Z coils (not shown in the figure). In some embodiments, the Z coils may be designed based on circular (Maxwell) coils, while the X coils and the Y coils may be designed on the basis of the saddle (Golay) coil configuration. The three sets of coils may be configured or used to generate three different magnetic fields that are used for position encoding. The gradient coils 202 may be configured or used to allow spatial encoding of MR signals for image construction. The gradient coils 202 may be connected with one or more of an X gradient amplifier 204, a Y gradient amplifier 205, or a Z gradient amplifier 206. One or more of the three amplifiers may be connected to a waveform generator 216. The waveform generator 216 may be configured or used to generate gradient waveforms that are applied to the X gradient amplifier 204, the Y gradient amplifier 204, and/or the Z gradient amplifier 204. An amplifier may be configured or used to amplify a waveform. An amplified waveform may be applied to one of the coils in the gradient coils 202 to generate a magnetic field in the X-axis, the Y-axis, or the Z-axis, respectively. The gradient coils 202 may be designed for either a close-bore MRI scanner or an open-bore MRI scanner. In some instances, all three sets of coils of the gradient coils 202 may be energized and three gradient fields may be generated thereby. In some embodiments of the present disclosure, the X coils and Y coils may be energized to generate the gradient fields in the X direction and the Y direction.

RF (radio frequency) coils 203 may be configured or used to generate a third magnetic field that is utilized to generate MR signals for image construction. In some instances, the RF coils 203 may include a transmitting coil and a receiving coil. In some embodiments, the RF coils 203 may be in connection with RF electronics 209 that may be configured or used as one or more integrated circuits (ICs) functioning as a waveform transmitter and/or a waveform receiver. The RF electronics 209 may be connected with an RF amplifier 207 and an analog-to-digital converter (ADC) 208. The waveform generator 216 may generate an RF signal. The RF signal may be first amplified by the RF amplifier 207, processed by the RF electronics 209, and applied on the RF coils 203 to generate a third magnetic field, in addition to the magnetic fields generated by, e.g., the main filed and shim coils 201 and the gradient coils 202. In some embodiments of the present disclosure, the waveform generator 201 may generate a series of RF waveforms periodically or aperiodically. For instance, the waveform generator 216 may generate an excitation RF pulse with a flip angle of 90° and multiple refocusing RF pulses with a flip angle of 180°. Note that the excitation RF pulse may have a flip angle other than 90°, e.g., any magnitude ranging from 0° to 180°. An excitation RF pulse with a flip angle of 90° is mentioned elsewhere in the present disclosure for illustration purposes, and is not intended to limit the scope of the present disclosure.

As described elsewhere in the present disclosure, the flip angle of a refocusing RF pulse may be of a value other than 180°. Furthermore, the waveform generator 216 may generate a series of RF waveforms periodically or aperiodically. For instance, the waveform generator 216 may generate an excitation RF pulse with a flip angle of 90° and multiple refocusing RF pulses with same flip angles or variable flip angles. The flip angle of the excitation RF pulse may be variable as well. The excitation RF pulse may be utilized to generate the third magnetic field, and with the application of one or more refocusing RF pulses, one or more MR signals may be generated. For instance, an echo train with multiple echoes may be generated. The echo train length (ETL) may be either fixed or variable. For instance, for a same tissue to be imaged, ETL may be fixed. For different tissues, ETL may be variable. Furthermore, even for a same tissue, ETL may be variable. The echo train may be received by the receiving coils of the RF coils 203. Then the echo train may be sent to the RF electronics 209, and transmitted to the ADC 208 for digitization. The echo train may be demodulated and filtered in the electronics 209. Subsequently, the echo train may be processed by an image processor 211, e.g., with the assistance of the CPU 213, to generate one or more images. A console 214 may communicate through a link with the CPU 213 and allow one or more operators to control the production and/or display of images on image display 212. The console 214 may include an input device, a control panel (not shown in the figure), etc. The input device may be a keyboard, a touch screen, a mouse, a remote controller, or the like, or any combination thereof.

The CPU 213 may be configured or used to control the production of the waveforms in the waveform generator 216, and the production of images in the image processor 211. The CPU 213 may be a central processing unit (CPU), an application-specific integrated circuit (ASIC), an application-specific instruction-set processor (ASIP), a graphics processing unit (GPU), a physics processing unit (PPU), a microcontroller unit, a digital signal processor (DSP), a field programmable gate array (FPGA), an ARM, or the like, or any combination thereof.

The data storage 215 may be configured or used to store received MR signals. When an MRI scan is completed and the whole data of a scanned object (e.g., a tissue or a specific part of a body) is acquired. A Fourier transform of the data may be performed by, without limitation to, the CPU 213, the image processor 211, or the like, or any combination thereof. After the transform is completed, one or more desired images may be generated. The images may be stored in the data storage 215. The images may be further conveyed to the image display 212 for display. A shim control 210 may be utilized to control the homogeneity of the main magnetic field generated by the main field and shim coils 201.

In some embodiments of the present disclosure, an improved or optimized flip angle schedule may be acquired according to one or more criteria described elsewhere in the present disclosure. A flip angle schedule may include a group of flip angles of refocusing RF pulses. The calculation of flip angles may be performed by the CPU 213. The refocusing RF pulses may be divided into a certain number of phases. Each phase may include one or more refocusing RF pulses. The flip angle(s) of refocusing RF pulse(s) of each phase may be calculated in accordance with one or more equations or functions. A signal evolution may be produced on the basis of the calculated flip angles of the refocusing RF pulses.

It should be noted that the above description of the MRI system is merely provided for the purposes of illustration, and not intended to limit the scope of the present disclosure. For persons having ordinary skills in the art, multiple variations and modifications may be made under the teaching of the present invention. However, those variations and modifications do not depart from the scope of the present disclosure.

Figure 3:
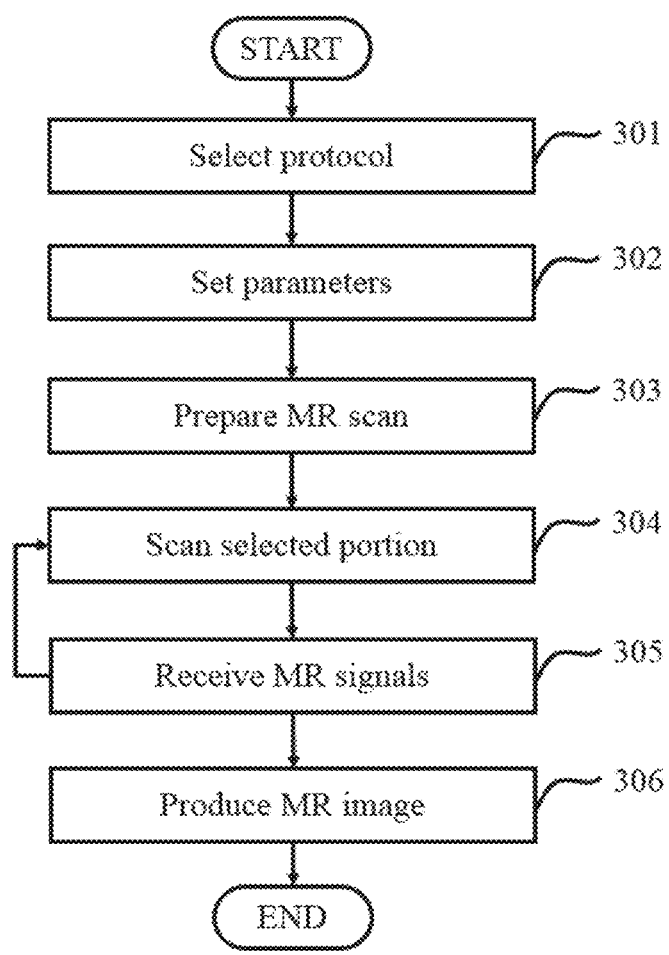
FIG. 3 is a flowchart illustrating a process for MRI according to some embodiments of the present disclosure.

FIG. 3 depicts a flowchart of an MR scan that may be performed according to some embodiments of the present disclosure. In step 301, one or more protocols may be selected. A protocol may be designed for one or more tissues to be imaged, diseases, and/or clinical scenarios. A protocol may contain a certain number of pulse sequences oriented in different planes and/or with different parameters. The pulse sequences may include spin echo sequences, gradient echo sequences, diffusion sequences, inversion recovery sequences, or the like, or any combination thereof. For instance, the spin echo sequences may include fast spin echo (FSE), turbo spin echo (TSE), rapid acquisition with relaxation enhancement (RARE), half-Fourier acquisition single-shot turbo spin-echo (HASTE), turbo gradient spin echo (TGSE), or the like, or any combination thereof. When an MR scan is to be conducted, an operator may select a protocol for the scan. For example, for a cranial scan, the operator may select any one of the protocols called "Routine Adult Brain," "MR Angiogram Circle of Willis," and many others. These protocols described above or other protocols may be stored in the data storage 215 as discussed in FIG. 2, or other storage devices (e.g., an external storage device or server accessible by the MR system 100).

Parameters may be set in step 302. The parameters may be set via the console 214 through a user interface that may be displayed on, e.g., the image display 212 as specified in FIG. 2. The parameters may include image contrast and/or ratio, a subject of interest, slice thickness, an imaging type (e.g., T1 weighted imaging, T2 weighted imaging, proton density weighted imaging, etc.), T1, T2, a spin echo type (spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), or the like, or any combination thereof.

According to some embodiments of the present disclosure, the term "phase" may refer to a segment, section, part or fragment of a series of flip angles (or a flip angle schedule) corresponding to an echo train divided according to some principles. The number of phase(s) and/or the number of echo(es) in each phase may depend on specific conditions. In some embodiments, an echo train may be divided into several phases according to considerations including, e.g., the characteristics of a reference signal schedule, a desired signal evolution, etc. Merely by way of example, the reference signal schedule of an echo train may be divided into three segments, regardless of what their values are or how their trends vary (e.g. firstly exponential decay, secondly essentially flat, and lastly exponential decay again), then the echo train may be divided into three phases accordingly. In some embodiments, the reference signal schedule may lack obvious characteristics on the basis of which to divide it into different phases. For example, only one or several specific echo(es) associated with resultant signal(s) of interest need to be paid attention to. For example, it is desired that the signals corresponding to two echoes meet one or more thresholds; the echo train may belong to a single phase so that the two echoes of interest are located in the same phase; the echo train may be divided into two or more phases, and the two echoes of interest may be located in a same phase or different phases. In some embodiments, there may be no reference signal schedule at all, and the number of phase(s) and/or the number of echo(es) in each phase may be determined based on, e.g., a random division, an equal division, a certain rule, or the like, or any combination thereof. The certain rule may include Arithmetic progression, Geometric progression, Cauchy sequence, Farey sequence, look-and-say sequence, or the like, or a variation thereof, or any combination thereof.

It should be noted that the above embodiments are for illustration purposes and not intended to limit the scope of the present disclosure. The determination of the number and length of the phase(s) may be variable, changeable, or adjustable based on the spirits of the present disclosure. For example, the number of phases in an echo train may be one, two, three, or more, or equal to the number of echoes. In some embodiments, several echoes may be located in one phase, and the remaining echoes belong to one or more other phases or are not assigned to a phase at all. However, those variations and modifications do not depart from the scope of the present disclosure.

Preparation for the MR scan may be performed in step 303. The preparation may include placing an object, e.g., a selected portion of a subject of interest, within the scanning area, setting the scanning range, tuning and matching shimming coils, adjusting a center frequency, adjusting transmitter attenuation/gain, adjusting signal reception attenuation/gain, setting dummy cycles, or the like, or any combination thereof.

The selected portion of a subject of interest may be scanned in step 304. The scanning may include localizer scans, calibration scans for parallel imaging, automatic pre-scan, or the like, or any combination thereof. For instance, the localizer scans may produce localizer images of low resolution and a large field of view (FOV). Such localizer images may be utilized in subsequent steps. In this step, one or more pulse sequences including, for example, an excitation RF pulse and a series of refocusing RF pulses, may be applied on the selected portion. The flip angles of the refocusing RF pulses may be either fixed or variable. In some embodiments of the present disclosure, the flip angles are not set in step 302 manually. Instead, the flip angles may be calculated automatically and an optimization procedure may be performed for the calculation of the flip angles until a desired signal evolution is achieved.

Generated MR signals may be received in step 305. Step 305 may be performed by the RF coils 203 as described in FIG. 2. The MR signals may correspond to one or more echo trains, or the like. It should be noted that step 305 and step 306 may be repeated until sufficient data to generate an image is acquired or an image is generated. One or more operations may be performed on the MR signals to produce images of the selected portion. The operations may include Fourier transform (FT), frequency encoding, phase encoding, or the like, or any combination thereof. For instance, Fourier transform may be a fast Fourier Transform (FFT), a 2-dimensional FT, a 3-dimensional FT, or the like, or any combination thereof. In step 306, one or more images of the selected portion may be produced. The images may be displayed on, e.g., the image display 212 (shown in FIG. 2), or other display devices (e.g., an external display device).

It should be noted that the flowchart described above is provided for the purposes of illustration, not intended to limit the scope of the present disclosure. For persons having ordinary skills in the art, multiple variations and modifications may be reduced to practice in the light of the present disclosure. However, those variations and modifications do not depart from the scope of the present disclosure. For instance, step 301, step 302, and step 303 may be performed sequentially at an order other than that described above in connection with FIG. 3. Alternatively, step 301, step 302, and step 303 may be performed concurrently.

MRI is a non-invasive imaging technique that uses a powerful main magnet field to align the nucleus spins in a subject (or a portion thereof). When the subject is exposed in a magnetic field (main magnet field B0), the nucleus spins of the subject tend to align with field B0, but may still precess at the Larmor frequency. The overall motion of the nucleus spins in the subject, subject to field B0, may be simplified as net magnetization (M) that is the averaged sum of many individual nucleus spins. The net magnetization M may be broken down into a longitudinal component (along the Z axis, aligned with field B0), and a transverse component (within the XY plane). With the effect of main magnet field B0, M may constitute a longitudinal magnetization vector in the macroscopic angle. A second magnetic field, RF field (field B1), may be applied to M, oscillating the Larmor frequency, and causing M to precess away from the field B0 direction. During the excitation by radio frequency, longitudinal magnetization may decrease and transverse magnetization may appear. Merely by way of example, if an excitation RF pulse with a 90° flip angle is applied, when the RF transmitter is turned off, there is no longitudinal magnetization any more, and only transverse magnetization exists. The transverse magnetization may induce a current signal in the RF receiving coils, and the induced current may be referred to as an MR signal.

Figure 4:
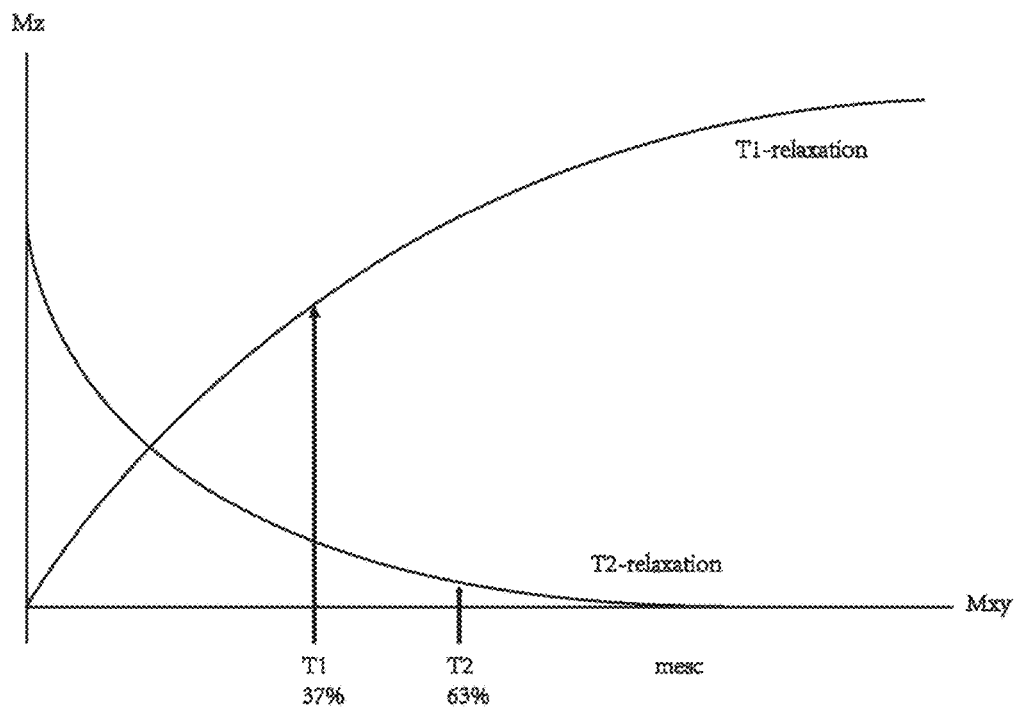
FIG. 4 is a graph illustrating exemplary T1-relaxation and exemplary T2-relaxation in a magnetic resonance imaging process according to some embodiments of the present disclosure.

After the RF excitation with a 90° excitation RF pulse is turned off, the transverse magnetization may decay. Note that the excitation RF pulse may have a flip angle other than 90°, e.g., any magnitude ranging from 0° to 180°. An excitation RF pulse with a flip angle of 90° is mentioned elsewhere in the present disclosure for illustration purposes, and is not intended to limit the scope of the present disclosure. In some embodiments, the decay may be approximated by an exponential curve, which is illustrated by the T2-relaxation shown in FIG. 4. The T2-relaxation (spin-spin relaxation) may be due to spins getting out of phase (or referred to as "dephase"). Since at least some nucleus spins may move together, their magnetic fields may interact with each other, and may cause a change in their precession rate. As these interactions are random and temporary, they may cause an accumulative loss in phase and lead to transverse magnetization decay. T2 may be defined as the time needed for the transverse magnetization to fall to 1/e or about 37% of its maximum value in FIG. 4. The T1-relaxation (spin-lattice relaxation) may result from energy exchange between the nucleus spins and their surrounding lattices, during which the spins go from a high energy state toward a thermal equilibrium state. As illustrated in FIG. 4, T1 may be defined as the time needed for the longitudinal magnetization to reach (1-1/e) or about 63% of its maximum value. At the same time, the longitudinal magnetization may recover following approximately an exponential form, which may be referred to as T1-relaxation shown in FIG. 4. It should be noted that for different subjects (e.g., tissues), their T1 and/or T2 are usually different from each other even when they are subject to the same magnet field. For example, with a 1.5 T filed strength, T1 of white matter, gray matter, and cerebrospinal fluid (CSF) of the brain are approximately 350~500, 400~600, 3000~4000 milliseconds, respectively. It should also be noted that T1 and T2 may be different from each other for a same tissue of a same subject under a same magnet filed. For example, with a 1.5 T filed strength, T1 of white matter of the brain may be about 350~500 milliseconds, while T2 of white matter of the brain may be about 90~100 milliseconds, which is shorter than the T1. T2-relaxation may exist regardless of whether there is a T1-relaxation. Some processes may result in or affect T2-relaxation but without affecting T1-relaxation. T1-relaxation may be slower than T2-relaxation. The T1 value may be longer than or equal to the corresponding T2 value.

The T2-relaxation may be exploited to generate an MR signal that may be used to image a subject. A spin echo based method may be used in an MRI system to prolong T2 relaxation time. The term "spin echo" or "spin echo sequence" generally refers to an echo or several echoes formed after the application of, for example, two RF pulses, an excitation RF pulse and a refocusing RF pulse. The spin echo and/or spin echo sequence includes single spin echo, multi-echo spin echo sequence, fast spin echo (FSE, or turbo spin echo, TSE) sequence, etc. In some embodiments of the single spin echo, a 90°-excitation RF pulse may tip the spins into the transverse plane. Then a refocusing RF pulse may turn the spins. The refocusing RF pulse may be used to reduce or prevent the dephasing caused by the non-uniformity of the main magnet field and preserve the real T2-relaxation. The single spin echo may generate one MR signal (e.g., an echo) during the course of the T2-relaxation. The MR signal may be used to generate an image. Some embodiments of the multi-spin echo sequence may be explained as follows: after the first echo is obtained, there may be an interval until the next repetition time (TR). By applying another refocusing RF pulse, another echo may occur and be detected, with the same phase encoding, to build another image. The other image may be of a different contrast, and may be useful in characterizing certain lesions. The multi-spin echo may build several images of several slices of the same positioning of a subject without increasing the overall acquisition time by using an interleaved scanning manner. The term "repetition time" or "TR" may refer to the time between the applications of two consecutive excitation RF pulses. The term "slice" here may refer to a planar region being excited by a spatial excitation RF pulse.

Figure 5:
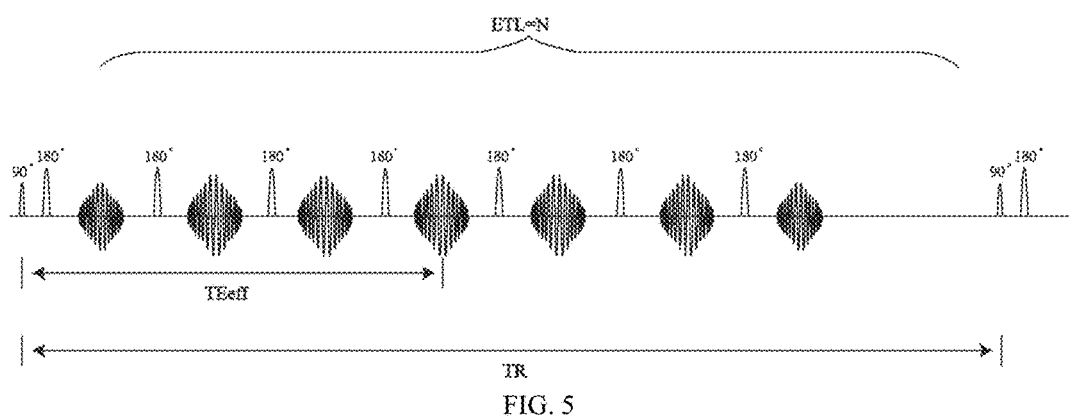
FIG. 5 is a graph illustrating an exemplary echo train for magnetic resonance imaging according to some embodiments of the present disclosure.

FIG. 5 is a graph of an exemplary flip angle schedule applicable in fast spin echo based magnetic resonance imaging according to some embodiments to the present disclosure. According to the fast spin echo technique, after the first echo is detected, within the time interval between the excitation RF pulse and the last refocusing RF pulse within a same TR, an echo train is detected, which may include one or more echoes, to fill the k-space lines in the same slice. Because multiple echoes may be detected within one TR, a reduced number of repetitions may be needed, the k-space may be filled faster, and the slice acquisition time may be reduced. This may be achieved by applying several 180° refocusing RF pulses to obtain an echo train. As described elsewhere in the present disclosure, the flip angle of a refocusing RF pulse may be of a value other than 180°. After each echo, the phase-encoding may be cancelled and a different phase-encoding may be applied to the following echo. The number of the echoes received within a same TR is called the echo train length (ETL). The echo train length (ETL) may be one, two, three, or more than three. In some embodiments, using refocusing RF pulses with flip angles of 180°, the specific absorption rate (SAR) may increase significantly and the T2 decay may be remarkable during imaging. In this condition, the ETL may need to be set short, e.g., no more than 30. In some embodiments, using refocusing RF pulses with variable flip angles, the ETL may be longer, e.g., more than 30. The ETL may be several hundred, or higher. As also illustrated in FIG. 5, in some embodiments of multi-spin echo, echo time (TE) is referred to as the time between the middle of an excitation RF pulse and the middle of the spin echo production. As used herein, "middle" may refer to when the intensity of an echo corresponding to a pulse, e.g., an excitation RF pulse, a refocusing RF pulse, arrives at a maximum value as illustrated in FIG. 5. For a multi-echo train, echo times may be denoted as TE1, TE2, etc. In some embodiments of fast spin echo, as the echoes corresponding to the central k-space lines are the ones that may determine image contrast, the time between the middle of an exciting RF pulse and the middle of the echoes corresponding to the central k-space is called effective echo time (effective TE, or $TE_{eff}$).

In some embodiments according to the present disclosure, the difference in the characteristic, e.g., T1 value, T2 value, and/or proton density (or spin density), among different subjects (e.g., different issues) may provide a basis to show an anatomic structure and/or pathological changes in magnetic resonance imaging. Several weighting imaging types may be used to emphasize above characteristics and build specific images. Exemplary imaging type may include T1 weighted imaging (T1WI), T2 weighted imaging (T2WI), proton density weighted imaging (PDWI), or the like, or any combination thereof. For example, in T1 weighted imaging, the differences in longitudinal relaxation of different subject are emphasized, but the effect of other characteristics, e.g., the differences in transverse relaxation, may be de-emphasized or depressed. T1 weighted imaging may have short TE and TR times. As another example, T2 weighted imaging exploits the transverse relaxation of the subjects, and de-emphasized or depressed other characteristics, e.g., longitudinal relaxation. T2 weighted imaging may require long TE and TR times. As still another example, proton density weighted imaging may reflect the proton (in the form of water or macromolecules, etc.) concentration of different subjects.

It should be noted that the above description of the spin echo sequence is merely provided for the purposes of illustration, and not intended to limit the scope of the present disclosure. For persons having ordinary skills in the art, multiple variations or modifications may be made under the teachings of the present disclosure. For example, the flip angle of a refocusing RF pulse may be of a value other than 180°; it may be any proper value chosen from 0~180°. As another example, TR or ETL may be changed or selected according to variations or modifications without departing from the scope of the present disclosure.

Figure 6:
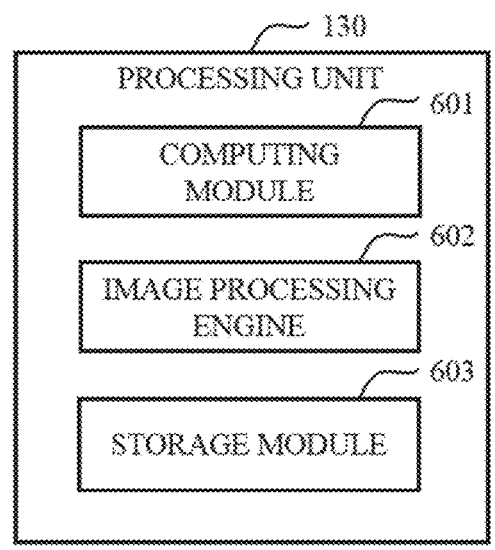
FIG. 6 is a block diagram illustrating a processing unit according to some embodiments of the present disclosure.

FIG. 6 is a block diagram illustrating the processing unit 130 according to some embodiments of the present disclosure. The processing unit 130 as illustrated in FIG. 1 may be configured or used for processing information before, during, or after an imaging procedure. Note that the construction of the processing unit 130 may have some other variations, and that FIG. 6 is provided for illustration purposes. The processing unit 130 may include a CPU. The CPU may be a central processing unit (CPU), an application-specific integrated circuit (ASIC), an application-specific instruction-set processor (ASIP), a graphics processing unit (GPU), a physics processing unit (PPU), a microcontroller unit, a digital signal processor (DSP), a field programmable gate array (FPGA), an ARM, or the like, or any combination thereof. As shown in FIG. 6, the processing unit 130 may include a computing module 601, an image processing engine 602, and a storage module 603.

The computing module 601 may be used for calculating different kinds of information received from the control unit 120 and/or display unit 140. The information from the control unit 120 may include information about the MRI scanner 110, the magnet unit 111, a patient position (e.g., within an MRI system), the RF unit 112, or the like, or any combination thereof. In some embodiments, the information may be a patient position, the main and/or gradient magnet intensity, the radio frequency phase and/or amplitude, and so on. The information from the display unit 140 may include information from a user and/or other external resource. Exemplary information from a user may include parameters regarding image contrast and/or ratio, a subject of interest (e.g., the type of tissue to be imaged, etc.), slice thickness, an imaging type (e.g., T1 weighted imaging, T2 weighted imaging, proton density weighted imaging, etc.), T1, T2, a spin echo type (e.g., spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), or the like, or any combination thereof.

The image processing engine 602 may be configured or used to process the data such as magnetic resonance (MR) signals acquired from the subject of interest and reconstruct them into an MR image. The image processing engine 602 may or may not include an image reconstruction block. The image processing engine 602 may spatially decode a magnetic resonance signal that has been spatially encoded by the magnetic field(s). The intensity or magnitude of the signal, and other properties such as a phase number, a relaxation time (T1 or T2), magnetization transfer, or the like, may be ascertained. The image processing engine 602 may employ different kinds of imaging reconstruction techniques for the image reconstruction procedure. The image reconstruction techniques may include Fourier reconstruction, constrained image reconstruction, regularized image reconstruction in parallel MRI, or the like, or a variation thereof, or any combination thereof.

The storage module 603 may be configured or used to store the information that may be used by the computing module 601 and/or the image processing engine 602. The information may include programs, software, algorithms, data, text, number, images and some other information. These examples are provided here for illustration purposes, and not intended to limit the scope of the present disclosure. Algorithms stored in the storage module 603 may include recursion, a bisection method, an exhaustive search (or brute-force search), a greedy algorithm, a divide and conquer algorithm, a dynamic programming method, an iterative method, a branch-and-bound algorithm, a backtracking algorithm, or the like, or any combination thereof.

It should be noted that the above description of the processing unit is merely provided for the purposes of illustration, and not intended to limit the scope of the present disclosure. For persons having ordinary skills in the art, multiple variations or modifications may be made under the teachings of the present disclosure. For example, the assembly and/or function of processing unit may be varied or changed. In some embodiments, the computing module 601 and the image processing engine 602 may share one storage module 603. While in some embodiments, the computing module 601 and the image processing engine 602 may have their own storage blocks, respectively. However, those variations and modifications do not depart from the scope of the present disclosure.

Figure 7:
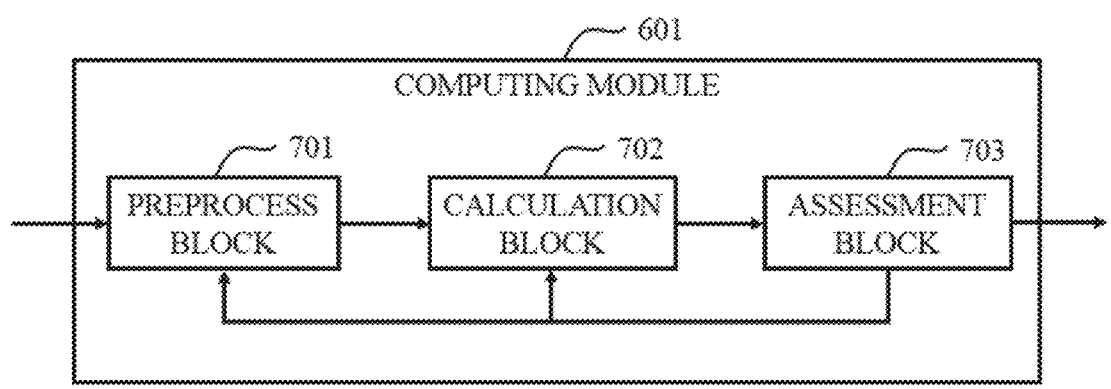
FIG. 7 is a block diagram illustrating a computing module according to some embodiments of the present disclosure.

FIG. 7 is a block diagram illustrating the computing module 601 according to some embodiments of the present disclosure. Note that the construction of the computing module 601 may have some other variations, and that FIG. 7 is provided for illustration purposes. With reference to FIG. 7, the computing module 601 may include a preprocess block 701, a calculation block 702, and an assessment block 703. The preprocess block 701 may be configured or used to execute some operations such as system initiation and/or parameter presetting. The calculation block 702 may be configured or used to calculate information based on the initial or preset information from the preprocess block 701. The information may include programs, software, algorithms, data, text, number, images and some other information. Exemplary algorithms may include recursion, a bisection method, an exhaustive search (or brute-force search), a greedy algorithm, a divide and conquer algorithm, a dynamic programming method, an iterative method, a branch-and-bound algorithm, a backtracking algorithm, or the like, or any combination thereof. The assessment block 703 may be configured or used to determine if the information from the calculation block 702 satisfy some requirements, criteria, thresholds or standards. In some embodiments, the requirements, criteria, thresholds or standards may be different in different phases of a flip angle schedule, as described elsewhere in the present disclosure.

A flip angle schedule may correspond to a single spin echo, multi-flip echoes, a fast spin echo, and so on. In this scene, the preprocess block 701 may be configured or used to preset some factors or parameters relative to the flip angle determination. The parameters may include image contrast and/or ratio, a subject of interest, slice thickness, an imaging type (e.g., T1 weighted imaging, T2 weighted imaging, proton density weighted imaging, etc.), T1, T2, a spin echo type (e.g., spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), or the like, or any combination thereof.

The calculation block 702 may include or be implemented on a device to calculate a flip angle sequence using different functions, and/or algorithms based on the initial information or condition preset in the preprocess block 701. The function(s) may include the Bloch equation, the EPG algorithm, a polynomial, a linear function, a trigonometric function, an anti-trigonometric function, an exponential function, a power function, a logarithmic function, or the like, or any combination thereof. Exemplary algorithms may include recursion, a bisection method, an exhaustive search (or brute-force search), a greedy algorithm, a divide and conquer algorithm, a dynamic programming method, an iterative method, a branch-and-bound algorithm, a backtracking algorithm, or the like, or any combination thereof. The algorithms may be executed on a software or program such as a general Math software. Exemplary software or program may include Matlab, Maple, Mathematica, MathCad, and/or numpy/scipy/sympy based on python and so on.

The assessment block 703 may assess if the flip angles calculated by the calculating block 702 satisfy a requirement, criterion, threshold, or standard. If the flip angles satisfy the requirement, criterion, threshold, or standard, it may be stored or output for further process or future use. If the flip angles do not satisfy the requirement, criterion, threshold, or standard, the MRI system may return to the preprocess block 701 and/or calculating block 702 and iterate the operations until a requirement, criterion, threshold, or standard is satisfied determined by, e.g., the assessment block 703. Note that the requirements, criteria, thresholds or standards may be different in different phases of a flip angle schedule, as described elsewhere in the present disclosure.

It should be noted that the above embodiments are exemplary and not intended to be limiting, and further embodiments also include those that will become apparent to those of ordinary skill in the art upon consulting the present disclosure. For example, the assembly and/or function of computing module 601 may be varied or changed. In some embodiments, additional components such as a storage block, interface block, a transmission block, etc., may be added into the computing 601 module as well. However, those variations or modifications do not depart from the scope of the present disclosure.

Figure 8:
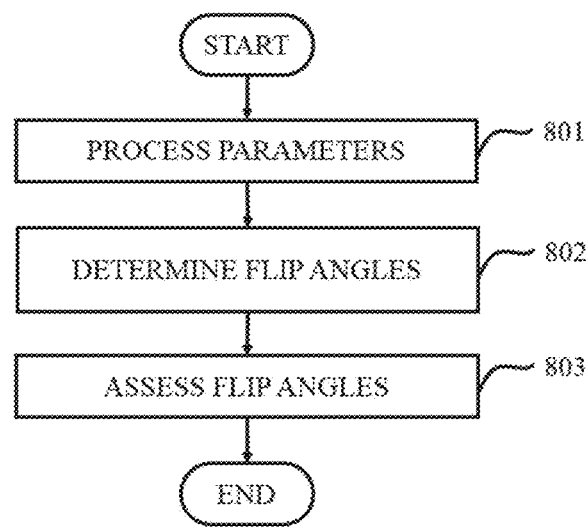
FIG. 8 is a flowchart illustrating a process for the determination of a flip angle schedule according to some embodiments of the present disclosure.

FIG. 8 is a flowchart illustrating a process for flip angle determination according to some embodiments of the present disclosure. In step 801, parameters for the calculation of a flip angle schedule may be set or processed. In some embodiments of the present disclosure, the parameters may include image contrast and/or ratio, a subject of interest, slice thickness, an imaging type (e.g., T1 weighted imaging, T2 weighted imaging, proton density weighted imaging, etc.), T1, T2, a spin echo type (e.g., spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), a function for describing the flip angle schedule or a portion thereof (e.g., a phase of an entire flip angle schedule), or the like, or any combination thereof.

The phases of a series of MR signals (e.g., a reference signal schedule, a signal evolution, etc.) may indicate the trend of the MR signal. For example, an MR signal may be one or more echo trains produced by refocusing RF pulses. Merely by way of example, an echo train may be divided into three phases, and in each phase, the MR signals may have a trend different from one or both of the other two phases. For instance, the trend of the MR signals in one phase is substantially a steady state indicating that the signals in that phase do not change significantly. Alternatively, the phases may be selected independent of the trend of the MR signals corresponding to the echo train. Therefore, the phases may be utilized to indicate the number of groups or phases into which the flip angles of the refocusing RF pulses are divided. If the echo train includes a plurality of phases, some of the parameters for different phases may be different, and some of the parameters for different phases may be the same. Merely by way of example, the T1 or T2 value for different phases of the echo train for the same tissue of a subject may be the same. As another example, the functions for different phases of the echo train for the same tissue of a subject may be different.

In some embodiments of the present disclosure, a phase of an echo train may have its own condition including an initial parameter (e.g., starting flip angle, ending flip angle, etc.), a function (e.g., a function for calculating the flip angle(s) of the phase, etc.), an algorithm (e.g., an algorithm for flip angle optimization), a reference signal schedule (e.g., a continuous signal evolution, a group of discrete reference signals, a target RMS (root mean square) in a phase, a mean value, or the like, or any combination thereof), a signal evolution selection criterion, or the like, or any combination thereof. In some embodiments, each echo train may have two or more phases. The conditions of different phases may be the same or different. In some embodiments, the impact of the flip angles of different phases on the resultant MR signals may be the same or different. For instance, an MR signal corresponding to an echo is obtained based on a refocusing RF pulse of a flip angle belonging to a specific phase, and the flip angle of the specific phase may have more impact on the resultant MR signals than the flip angles of another phase. The flip angles of the different phases may be processed sequentially, randomly, simultaneously, etc. In some embodiments, the phase(s) with higher impact may be seen as priority phase(s). The non-priority phase(s) may be subject to less or no restrictions and may be adjusted as needed to ensure that the priority phase(s) attain(s) its or their corresponding condition(s). To illustrate the present disclosure more clearly, some exemplary embodiments of flip angle determination may be given below in connection with the exemplary context that there are three phases in one echo train and MR signals are obtained corresponding to one or more echoes in the middle phase. In this exemplary context, the parameters of the first phase and the last phase may be changed freely, while the parameters of the middle phase may need to satisfy certain criteria. Exemplary criteria may be that a flip angle schedule of the phase is selected such that the resultant MR signals are close enough to a reference signal schedule. More description in this regard may be found elsewhere in the present disclosure.

It should be noted that the above embodiments are for illustration purposes and not intended to limit the scope of the present disclosure. The embodiments may be variable, changeable or adjustable based on the spirits of the present disclosure. For example, flip angle calculation in different phases may be based on a same function or different functions chosen from, for example, the Bloch equation, the EPG algorithm, a polynomial, a linear function, a trigonometric function, an anti-trigonometric function, an exponential function, a power function, a logarithmic function, or the like, or any combination thereof. As another example, the phases and/or the condition or parameters of phases may be given different weight. However, those variations and modifications do not depart from the scope of the present disclosure.

One or more flip angles of the refocusing RF signals may be determined in step 802. In some embodiments of the present disclosure, the flip angles may be determined based on, e.g., the function(s), the initial conditions including the starting flip angle, the ending flip angle in a phase, or the like, or any combination thereof. The function(s) may include the Bloch equation, the EPG algorithm, a polynomial, a linear function, a trigonometric function, an anti-trigonometric function, an exponential function, a power function, a logarithmic function, or the like, or any combination thereof.

In step 803, an assessment may be performed to determine whether one or more desired flip angles are obtained. The assessment may be based on one or more signals corresponding to the flip angles determined in step 802. For instance, a signal may be determined based on a relationship with a flip angle. The relationship may be described by, e.g., the Bloch equation, the EPG algorithm, or the like, or any combination thereof. The assessment may be based on a comparison between a signal evolution and a reference signal schedule, while the signal evolution is produced on the basis of the flip angles determined in step 802 and the relationship as mentioned. A signal evolution may include one or more signals.

It should be noted that in some embodiments of the present disclosure, both the signal evolution and the reference signal schedule may correspond to one or more echo trains respectively, and an echo train may be divided into one or more phases. The signal evolution may be one or more echo trains produced by one or more refocusing RF pulses with flip angles calculated in step 802. The reference signal schedule may correspond to one or more echo trains with an expected signal intensity of every echo. Alternatively, the reference signal schedule may be a loose restriction on the signal intensity of one or more echoes, e.g., the signal intensity of the starting echo and that of the ending echo of each phase of an echo train, the ending echo of each phase of an echo train, an nth echo in the echo train, or the like, or any combination thereof. As a further example, the reference signal schedule specifies a desired signal intensity, without specifying how or when the corresponding echo (the echo that corresponding to the signal of the specified intensity) occurs in the echo train. In some embodiments, the reference signal schedule may include a restriction on the trend of each phase in one or more echo trains. The trend may be increasing, decreasing, steady state, or the like. It should be noted that the trend restriction may be applied on any number of phases in the one or more echo trains.

Still in some embodiments, the reference signal schedule is not provided. For instance, several flip angle schedules may be calculated, and one of them is selected based on the resultant signal evolutions. The result signal evolutions may be determined based on a relationship with a flip angle schedule. The relationship may be described by, e.g., the Bloch equation, the EPG algorithm, or the like, or any combination thereof. In some embodiments, a flip angle schedule associated with a desired signal evolution is selected. The signal evolution may include one or more signals. A desired signal evolution may be a signal of a desired intensity, a signal evolution or a portion (or a phase) thereof with a desired trend, or the like, or any combination thereof. For instance, a desired trend may be that a portion of the signal evolution is essentially flat, the signal evolution or a portion thereof changes at a certain rate or at a rate higher or lower than a threshold. In some embodiments, a flip angle schedule that may lead to a desired contrast among two or more tissues (e.g., the tissues scanned simultaneously in one scanning or image acquisition) in the resultant signals may be selected. Merely by way of example, when the brain of a subject is scanned, the grey matter, the white matter, and the CSF may be scanned simultaneously, and a flip angle schedule that may provide a desired contrast among these tissues in the resultant signals may be selected. In some embodiments, a flip angle schedule that may lead to an MR image of desirable quality may be selected. Image quality may be assessed based on image contrast, resolution, mean squared error (MSE), signal to noise rate (SNR), artifacts, or the like, or any combination thereof.

It should be noted that the flowchart described above is provided for the purposes of illustration, and may not intended to limit the scope the present disclosure. For persons having ordinary skills in the art, a certain amount of variations and modifications may be reduced under guidance of the present disclosure. Those variations do not depart from the scope of the present disclosure.

Figure 9:
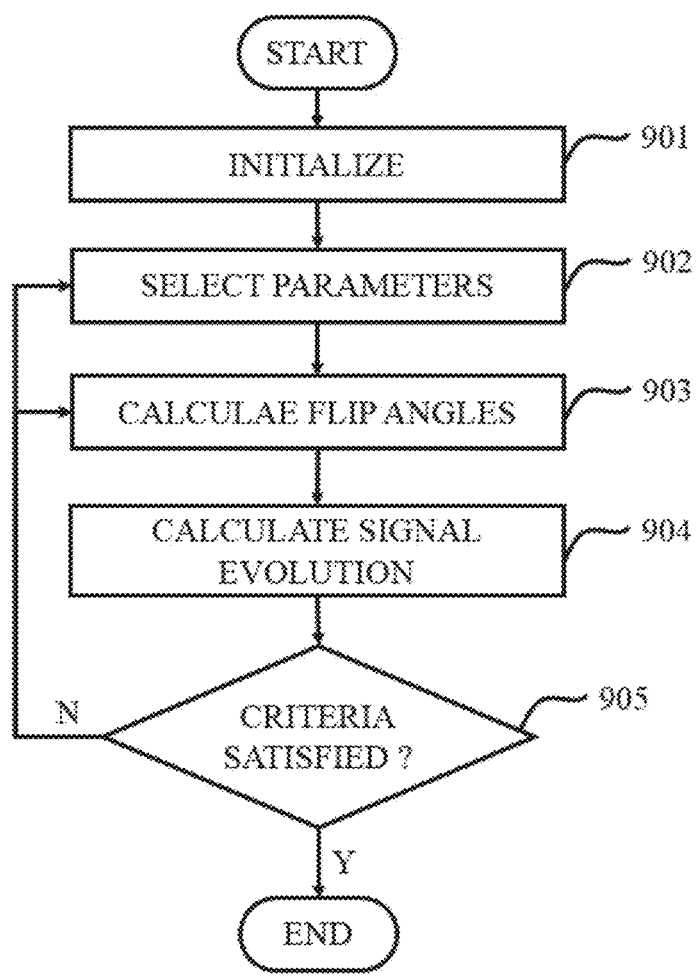
FIG. 9 is a flowchart illustrating a process for the determination of a flip angle schedule according to some embodiments of the present disclosure.

FIG. 9 is a flowchart illustrating an exemplary process for determining a flip angle schedule according to some embodiments of the present disclosure. In step 901, an initiation may be performed. In some embodiments of the present disclosure, the initiation may include setting an initial condition including, e.g., one or more of parameters. Exemplary parameters may include image contrast and/or ratio, a subject of interest, slice thickness, an imaging type (e.g., T1 weighted imaging, T2 weighted imaging, proton density weighted imaging, etc.), T1, T2, a spin echo type (spin echo, fast spin echo (FSE), fast recovery FSE, single shot FSE, gradient recalled echo, fast imaging with steady-state procession, and so on), flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), a function for describing the flip angle schedule or a portion thereof (e.g., a phase of an entire flip angle schedule), a reference signal schedule, or the like, or any combination thereof. The function(s) may include the Bloch equation, the EPG algorithm, a polynomial, a linear function, a trigonometric function, an anti-trigonometric function, an exponential function, a power function, a logarithmic function, or the like, or any combination thereof.

The function of the flip angle schedule provided in the initiation may include one or more factors or parameters to be determined. In some embodiments, the factors or parameters may be determined based on the assessment as discussed in connection with FIG. 8. As already described, the assessment may be based on a resultant signal evolution corresponding to a flip angle schedule. In some embodiments, the assessment may be based on whether one or more resultant signals of a resultant evolution satisfy a requirement, criterion, threshold, or standard. In some embodiments, the assessment may be based on whether a section (e.g., a phase or a portion) of a resultant evolution satisfy a requirement, criterion, threshold, or standard. In some embodiments, the assessment may be based on a comparison among several resultant signal evolutions. In some embodiments, the assessment may be based on a comparison between the resultant signal evolutions with a reference signal schedule.

In some embodiments, the one or more factors or parameters to be determined may include a starting flip angle, an ending flip angle, and a characteristic parameter. In some embodiments, the one or more factors or parameters to be determined may include more than one characteristic parameter. For illustration purposes, the following description is provided assuming the exemplary embodiment of one characteristic parameter. It is understood that this is not intended to limit the scope of the present disclosure to the exemplary embodiments of one characteristic parameter. The initial condition may include information regarding at least one of these factors or parameters. Merely by way of example, a starting flip angle, and an ending flip angle, and a characteristic parameter for a phase of the flip angle schedule may be set in the initial condition, and the remaining flip angles in a portion of or the entire phase may be calculated or derived based on the initial condition and the function. As used herein, a starting flip angle for a phase of a flip angle schedule may refer to the flip angle corresponding to the starting point of a phase of MR signals (e.g., a reference signal schedule, an echo train); an ending flip angle for the same phase of a flip angle schedule may refer to the flip angle corresponding to the ending point of the phase of MR signals (e.g., a reference signal schedule, an echo train). In some embodiments, the initial condition may include a range for the starting flip angle and/or the ending flip angle, and the magnitude of the starting flip angle and the ending flip angle may be limited to the range. The limitation of the starting flip angle and the ending flip angle may contribute to a reduction of the motion artifact. When the imaging of a motion is desired, e.g., in angiography, large flip angles may be utilized to capture images for a flowing or moving subject (e.g., flowing or moving tissues). This may be achieved by setting the lower limit of the range high. When the imaging of a motion is undesired, e.g., in brain imaging, small flip angles may be utilized to reduce or eliminate the motion artifact. This may be achieved by setting the lower limit of the range low. Limiting the upper limit of the range may reduce, e.g., SAR.

In some embodiments of the present disclosure, e.g., in a cervical spine imaging, the maximum flip angle of an echo train may be set to be lower than 120°. When variable flip angles are applied in fast spin echo imaging, signals from flowing CSF may be low, and its interference with the observation of the spinal tissues may be reduced.

In some embodiments of the present disclosure, e.g., in a knee join imaging, the maximum flip angle of an echo train may be set to be lower than 120°. When variable flip angles are applied in fast spin echo imaging, signals from a blood vessel may be reduced due to the reduced motion artifact caused by vascular pulsation.

In some embodiments of the present disclosure, e.g., in an abdominal imaging, the imaging of the liver may be interfered by the breathing movement. Such an interference may be reduced by setting the minimum flip angle to be greater than 80°.

Given that SAR may increase as the flip angle increases, the maximum flip angle of a flip angle schedule or a phase thereof may be controlled to restrict or reduce the maximum SAR. Merely by way of example, in a hip joint imaging, SAR is high. Thus, a maximum flip angle (e.g., 140°) may be predefined to restrict SAR.

It should be understood that a reference signal schedule, as well as the signal evolution, may be one or more echo trains and each echo train may include one or more echoes, each echo train may be divided into one or more phases. For instance, the signal evolution may be one or more echo trains produced by one or more refocusing RF pulses with flip angles calculated in step 903. The reference signal schedule may be one or more echo trains with an expected signal intensity of every echo. Alternatively, the reference signal schedule may be a loose restriction on the signal intensity of one or more specific echoes, e.g., the signal intensity of the starting echo and the ending echo of each phase of an echo train, the signal intensity of the ending echo of each phase of an echo train, an nth echo in the echo train, or the like, or any combination thereof. As a further example, the reference signal schedule specifies a desired signal intensity, without specifying how or when the corresponding echo (the echo that corresponding to the signal of the specified intensity) occurs in the echo train. It should be noted that the restrictions may be signal intensity restrictions on any number of the echoes. In alternative embodiments, the reference signal schedule does not specify signal intensity of any echoes; instead, the reference signal schedule may specify the trend of one or more phases in an echo train. The trend may be increasing, decreasing, steady state, or the like. It should be noted that the trend restriction may be applied on any number of phases in the one or more echo trains. Still in some embodiments, no reference signal schedule is provided. Under this circumstance, a group of desired flip angles may be selected from multiple signal evolutions. See relevant description elsewhere in the present disclosure.

In some embodiments, the reference signal schedule may be selected or defined by a user. In some embodiments, the reference signal schedule may be selected by an MRI system based on information provided by a user. Exemplary information may include an actual imaging to be performed, the subject to be imaged, T1 of the subject, T2 of the subject, the proton density of a desired subject, or the like, or any combination thereof. For instance, the reference signal schedule (e.g., an echo train) may be divided into 1 phase, 2 phases, 3 phases, 4 phases, or theoretically any number of phases. If the reference signal schedule includes a plurality of phases, the functions for at least two of the plurality of phases may be different indicated by differences in at least one of the starting flip angle, the ending flip angle, and the characteristic parameter. In some embodiments, for two adjoining phases (one preceding the other), the ending flip angle of the preceding phase may be the same as the starting flip angle of the phase following the preceding phase. See, for example, FIGS. 15A-15C. The functions for at least two of the phases may be in a same form. For instance, the functions for at least two of the phases may be in the form of the Bloch equation, the EPG algorithm, a polynomial, a linear function, a trigonometric function, an anti-trigonometric function, an exponential function, a power function, a logarithmic function, or the like, or any combination thereof.

The MRI system may perform a parameter selection in step 902. The parameters in step 902 may be different from the parameters described in step 901. In some embodiments of the present disclosure, the number of phases may be utilized to indicate how an echo train is divided. In some embodiments, for two adjoining phases (one preceding the other), the ending flip angle of the preceding phase may be utilized as the starting flip angle of the phase following the preceding phase. The functions for flip angle calculation may include the Bloch equation, the EPG algorithm, a polynomial, a linear function, a trigonometric function, an anti-trigonometric function, an exponential function, a power function, a logarithmic function, or the like, or any combination thereof.

In step 903, the calculation of flip angles may be performed. The calculation may be based on the parameters including the function(s) described in step 901. A group of flip angles may be generated in step 903.

In some embodiments of the present disclosure, the echo train may be divided into one or more phases. In a phase, the flip angles of the refocusing RF pulses may vary in accordance with, e.g., an exponential function. Merely by way of example, assuming that N is the echo train length (ETL), $\alpha_0$ is the starting flip angle of a phase, $\alpha_{N-1}$ is the ending flip angle of that phase, the flip angles in one phase may be described using the following functions: if $\alpha_{N-1} \geq \alpha_0$, the remaining flip angles of the phase may be calculated by:

$$\alpha_n = \alpha_0 + (\alpha_{N-1} - \alpha_0) \cdot \frac{e^{\left(\frac{n^2}{P^2}\right)} - 1}{e^{\left(\frac{(N-1)^2}{P^2}\right)} - 1}, \quad \text{(Equation 1)}$$

if $\alpha_0 > \alpha_{N-1}$, the remaining flip angles of the phase may be calculated by:

$$\alpha_n = \alpha_{N-1} + (\alpha_0 - \alpha_{N-1}) \cdot \frac{e^{\left(\frac{(N-1-n)^2}{P^2}\right)} - 1}{e^{\left(\frac{(N-1)^2}{P^2}\right)} - 1}, \quad \text{(Equation 2)}$$

Where n=0, 1, . . . , N−1.

P is a characteristic parameter. In some embodiments, P may control or affect the rate of the flip angles change around the starting point and the ending point in a phase. P may be a real number that is greater than 1. P of one phase may be different from that of another phase.

In some embodiments of the present disclosure, the echo train may be divided into one or more phases. In a phase, the flip angles of the refocusing RF pulses may vary in accordance with, e.g., a linear function. Merely by way of example, assuming that N is the echo train length (ETL), $\alpha_0$ is the starting flip angle of a phase, $\alpha_{N-1}$ is the ending flip angle of that phase, the flip angles in one phase may be described using the following functions:

$$\alpha_n = \frac{n}{N-1}(\alpha_{N-1} - \alpha_0) + \alpha_0, \quad \text{(Equation 3)}$$

Where n=0, 1, . . . , N−1.

In some embodiments of the present disclosure, the echo train may be divided into one or more phases. In each phase, the flip angles of the refocusing RF pulses may vary in accordance with, e.g., a polynomial. Merely by way of example, assuming that N is the echo train length (ETL), $\alpha_0$ is the starting flip angle of a phase, $\alpha_{N-1}$ is the ending flip angle of that phase, the flip angles in one phase may be described using the following functions:

$$\alpha_n = \alpha_0 + \Sigma_{l=1}^{K} P_l \cdot n^l, \quad \text{(Equation 4)}$$

Where n=0, 1, . . . , N−1. P=[$P_1, P_2, \ldots, P_K$] is a vector of characteristic parameters. In some embodiments, K may be an integer less than 10. $P_1, P_2 \ldots P_K$ may be selected so that the flip angle schedule may be either monotonically increasing or monotonically decreasing, and meet the criteria that:

$$\alpha_{N-1} = \alpha_0 + \Sigma_{l=1}^{K} P_l (N-1)^l, \quad \text{(Equation 5)}$$

In step 904, a signal evolution (e.g., an echo train) may be calculated based on the flip angles determined in step 903. In some embodiments of the present disclosure, the relationship between the flip angles and the signal evolution may be described based on, e.g., the Bloch equation, the EPG algorithm, or the like, or any combination thereof. In some embodiments, the signal evolution calculation may be calculated in accordance of T1 and T2 of a desired tissue to be subject to the MRI procedure. Alternatively, the calculation may also be performed regardless of the relaxation time of a tissue.

In step 905, an assessment of a flip angle schedule may be made based on a resultant signal evolution corresponding to the calculated flip angle schedule. In some embodiments, the assessment may be based on whether one or more resultant signals of a resultant evolution satisfy a requirement, criterion, threshold, or standard. In some embodiments, the assessment may be based on whether a section (e.g., a phase or a portion) of a resultant evolution satisfy a requirement, criterion, threshold, or standard. In some embodiments, the assessment may be based on a comparison among several resultant signal evolutions. In some embodiments, an assessment may be made based on a comparison between the resultant signal evolutions with a reference signal schedule. See further description elsewhere in the present disclosure, for example, relevant descriptions in connection with FIG. 8.

Merely by way of example, the assessment may be made based on a comparison between the signal evolution obtained in step 904 and a reference signal schedule according to one or more criteria. Exemplary criteria may be the L1 norm, the L2 norm, a standard deviation, etc.

In some embodiments of the present disclosure, the form of the L1 norm may be described below, assuming that S(n) is the signal value calculated in step 904 for echo n, and $S_{exp}(n)$ is the expectation signal intensity (the reference signal) for echo n, N is the echo train length (ETL):

$$d=\Sigma_n|S(n)-S_{exp}(n)|, \quad \text{(Equation 6)}$$

Where n=0, 1, . . . , N−1.

In some embodiments of the present disclosure, the form of the L2 norm may be described below, assuming that S(n) is the signal value calculated in step 904 for echo n, and $S_{exp}(n)$ is the expectation signal value (the reference signal) for echo n, N is the echo train length (ETL):

$$d=\Sigma_n|S(n)-S_{exp}(n)|^2, \quad \text{(Equation 7)}$$

Where n=0, 1, . . . , N−1.

In some embodiments of the present disclosure, the comparison may be based on the equation expressed below, assuming E is a constant whose value is an expected signal or the mean value of $S_{exp}(n)$:

$$d=\sqrt{\Sigma_n|S(n)-\Sigma|^2}, \quad \text{(Equation 8)}$$

Where n=0, 1, . . . , N−1.

In some embodiments of the present disclosure, the comparison may be based on variance as expressed in the equation below, assuming E is a constant whose value is an expected signal or the mean value of $S_{exp}(n)$:

$$d = \frac{1}{N-1}\sum_n (S(n)-E)^2, \quad \text{(Equation 9)}$$

Where n=0, 1, . . . , N−1.

In some embodiments of the present disclosure, the comparison equation may be expressed by standard deviation, assuming E is a constant whose value is an expected signal or the mean value of $S_{exp}(n)$:

$$d = \sqrt{\frac{1}{N}\sum_n (S(n)-E)^2}, \quad \text{(Equation 10)}$$

Where n=0, 1, . . . , N−1.

In some embodiments, the signal intensity of one or more several echoes are desired or specified, the assessment or comparison may be based on the signal value(s) calculated in step 904 and the desired or specified signal intensity at the corresponding echoes.

Note that the above exemplary equations for assessment or comparison are merely for illustration and not intended to limit the scope of the present disclosure. Some variation, deformation or modification of the comparison equations may be obvious to the persons have ordinary skill in the art. For example, the assessment or comparison may be based on a mean-squared error, a root-mean-square error, etc. As another example, an echo may be weighted and a coefficient may be added into the comparison equations.

It should be noted that the assessment (regardless of whether a reference signal schedule is used, or the specific form of the reference signal schedule used) may be performed in each phase either sequentially or concurrently. If the criteria is met in step 905, the calculation of the flip angles may be terminated. Otherwise, a new group of flip angles may be calculated by repeating steps 902-904. The number of iterations may be either fixed or variable. In some instances, the number of iterations may be adaptive. The new group of flip angles may be calculated by adjusting parameters including, e.g., the starting flip angle $\alpha_0$, the ending flip angle $\alpha_{N-1}$ and the characteristic parameter P of each phase as described in equation 1 and equation 2. The MRI system may adjust any one of the three parameters, or any two of the three parameters, or all three parameters to calculate a new group of flip angles. It should be further noted that the parameters may be adjusted in step 902. Merely by way of example, parameters including, e.g., the starting flip angle, the ending flip angle, the characteristic parameter P, may be adjusted using an algorithm. Exemplary algorithms may include recursion, a bisection method, an exhaustive search (or brute-force search), a greedy algorithm, a divide and conquer algorithm, a dynamic programming method, an iterative method, a branch-and-bound algorithm, a backtracking algorithm, or the like, or any combination thereof. In some embodiments, in each phase the starting flip angle $\alpha_0$ may be the maximum flip angle and the ending flip angle $\alpha_{N-1}$ may be the minimum flip angle in the phase, vice versa. The minimum flip angle may be within a range to reduce the artifact, while the maximum flip angle may be within a range to reduce SAR.

Figure 10:
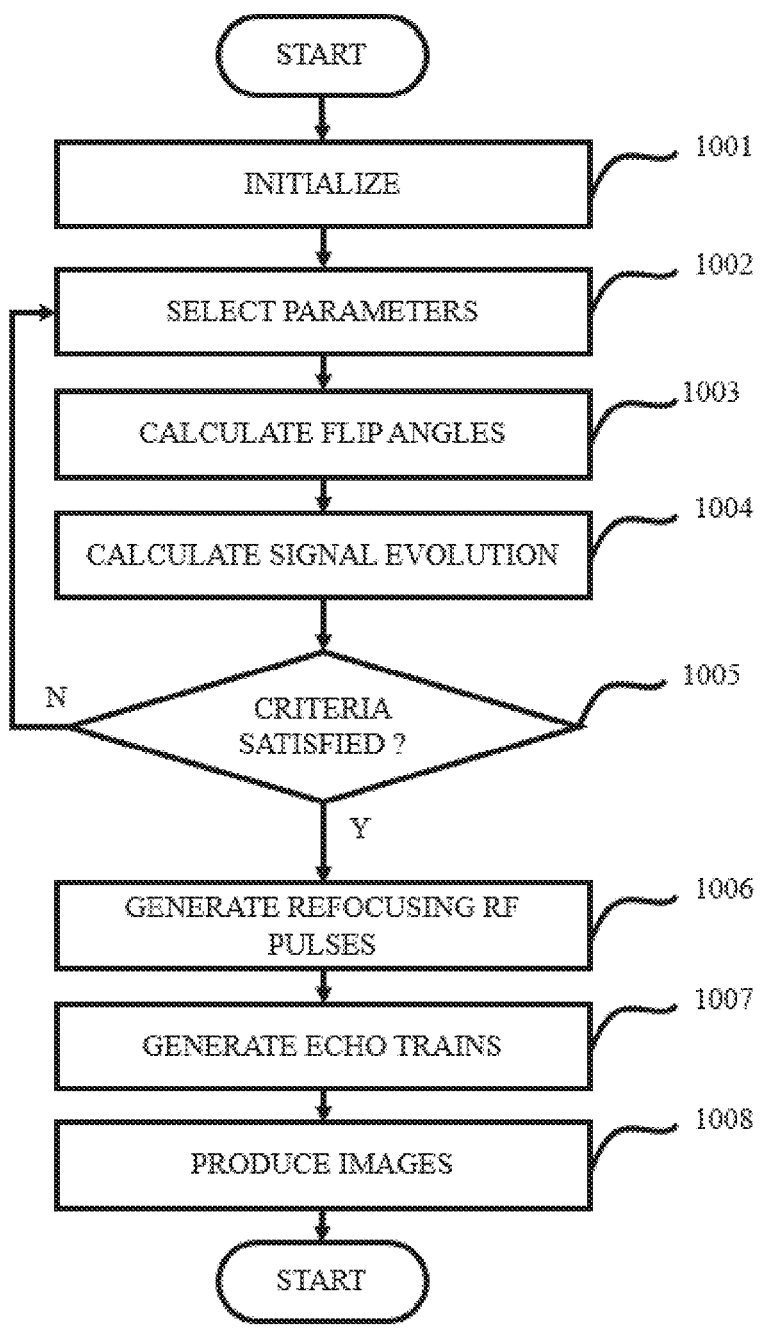
FIG. 10 is a flowchart illustrating a process for MRI according to some embodiments of the present disclosure.

FIG. 10 is a flowchart illustrating an exemplary process for MR imaging according to some embodiments of the present disclosure. In step 1001, an initiation may be performed. In some embodiments of the present disclosure, the initiation may include setting an initial condition including, e.g., one or more parameters. The parameters may include image contrast and/or ratio, a subject of interest, slice thickness, an imaging type (e.g., T1 weighted imaging, T2 weighted imaging, proton density weighted imaging, etc.), T1, T2, a spin echo type (spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), a function for describing the flip angle schedule or a portion thereof (e.g., a phase of an entire flip angle schedule), a reference signal schedule, or the like, or any combination thereof. The function(s) may include the Bloch equation, the EPG algorithm, a polynomial, a linear function, a trigonometric function, an anti-trigonometric function, an exponential function, a power function, a logarithmic function, or the like, or any combination thereof.

The function of the flip angle schedule provided in the initiation may include one or more factors or parameters to be determined. In some embodiments, the factors or parameters may be determined based on the assessment as discussed in connection with FIG. 8. As already described, the assessment may be based on a resultant signal evolution corresponding to a flip angle schedule. In some embodiments, the assessment may be based on whether one or more resultant signals of a resultant evolution satisfy a requirement, criterion, threshold, or standard. In some embodiments, the assessment may be based on whether a section (e.g., a phase or a portion) of a resultant evolution satisfy a requirement, criterion, threshold, or standard. In some embodiments, the assessment may be based on a comparison among several resultant signal evolutions. In some embodiments, the assessment may be based on a comparison between the resultant signal evolutions with a reference signal schedule.

In some embodiments, the one or more factors or parameters to be determined may include a starting flip angle, an ending flip angle, and a characteristic parameter. In some embodiments, the one or more factors or parameters to be determined may include more than one characteristic parameter. For illustration purposes, the following description is provided assuming the exemplary embodiment of one characteristic parameter. It is understood that this is not intended to limit the scope of the present disclosure to the exemplary embodiments of one characteristic parameter. The initial condition may include information regarding at least one of these factors or parameters. Merely by way of example, a starting flip angle, and an ending flip angle, and a characteristic parameter for a phase of the flip angle schedule may be set in the initial condition, and the remaining flip angles in a portion of or the entire phase may be calculated or derived based on the initial condition and the function. As used herein, a starting flip angle for a phase of a flip angle schedule may refer to the flip angle corresponding to the starting point of a phase of MR signals (e.g., a reference signal schedule, an echo train); an ending flip angle for the same phase of a flip angle schedule may refer to the flip angle corresponding to the ending point of the phase of MR signals (e.g., a reference signal schedule, an echo train). In some embodiments, the initial condition may include a range for the starting flip angle and/or the ending flip angle, and the magnitude of the starting flip angle and the ending flip angle may be limited to the range. The limitation of the starting flip angle and the ending flip angle may contribute to a reduction of the motion artifact. When the imaging of a motion is desired, e.g., in angiography, large flip angles may be utilized to capture images for a flowing or moving subject (e.g., flowing or moving tissues). This may be achieved by setting the lower limit of the range high. When the imaging of a motion is undesired, e.g., in brain imaging, small flip angles may be utilized to reduce or eliminate the motion artifact. This may be achieved by setting the lower limit of the range low. Limiting the upper limit of the range may reduce, e.g., SAR.

The MRI system may perform a parameter selection in step 1002 according to the parameters set in step 1001. It should be noted that in some instances, TR, TE, T1 and T2 may be set in step 1002. In some embodiments of the present disclosure, the number of phases may be utilized to indicate how an echo train is divided. For example, the echo train may be divided into 1 phase, 2 phases, 3 phases, 4 phases, or theoretically any number of phases. The functions for flip angle calculation may include the Bloch equation, the EPG algorithm, a polynomial, a linear function, a trigonometric function, an anti-trigonometric function, an exponential function, a power function, a logarithmic function, or the like, or any combination thereof.

In step 1003, the calculation of flip angles may be performed. The calculation may be based on the parameters described in step 1002. A group of flip angles may be generated in step 1003.

In step 1004, a signal evolution (e.g., an echo train) may be calculated based on the flip angles determined in step 1003. In some embodiments of the present disclosure, the relationship between the flip angles and the signal evolution may be described based on, e.g., the Bloch equation, the EPG algorithm, or the like, or any combination thereof. In some embodiments, the signal evolution calculation may be calculated in accordance of T1 and T2 of a desired tissue to be subject to the MRI procedure. Alternatively, the calculation may also be performed regardless of the relaxation time of a tissue.

As already described, an assessment of a flip angle schedule may be made based on a resultant signal evolution corresponding to the calculated flip angle schedule. In some embodiments, the assessment may be based on whether one or more resultant signals of a resultant evolution satisfy a requirement, criterion, threshold, or standard. In some embodiments, the assessment may be based on whether a section (e.g., a phase or a portion) of a resultant evolution satisfy a requirement, criterion, threshold, or standard. In some embodiments, the assessment may be based on a comparison among several resultant signal evolutions. In some embodiments, an assessment may be made based on a comparison between the resultant signal evolutions with a reference signal schedule. See further description elsewhere in the present disclosure, for example, relevant descriptions in connection with FIG. 8.

Merely by way of example, the assessment may be made based on a comparison between the signal evolution obtained in step 1004 and a reference signal schedule according to one or more criteria. Exemplary criteria may be the L1 norm, the L2 norm, a standard deviation, etc.

It should be noted that the assessment (regardless of whether a reference signal schedule is used, or the specific form of the reference signal schedule used) may be performed in each phase either sequentially or concurrently. If the criteria is met in step 1005, the calculation of the flip angles may be terminated. Otherwise, a new group of flip angles may be calculated by repeating steps 1002-1004. The number of iterations may be either fixed or variable. In some instances, the number of iterations may be adaptive. It should be noted that in some embodiments of the present disclosure, if the criteria is not satisfied in step 1005, the MRI system may return to steps 1002 and 1003 and calculate a new group of flip angles by adjusting the three parameters, the starting flip angle $\alpha_0$, the ending flip angle $\alpha_{N-1}$ and the characteristic parameter P of each phase as described in equation 1 and equation 2. The MRI system may adjust any one of the three parameters, or any two of the three parameters, or all three parameters to calculate a new group of flip angles. It should be further noted that the parameters may be adjust in step 1002. Merely by way of example, parameters including, e.g., the starting flip angle, the ending flip angle, the characteristic parameter P, may be adjusted using an algorithm. Exemplary algorithms may include recursion, a bisection method, an exhaustive search (or brute-force search), a greedy algorithm, a divide and conquer algorithm, a dynamic programming method, an iterative method, a branch-and-bound algorithm, a backtracking algorithm, or the like, or any combination thereof. It should be still further noted that in each phase the starting flip angle $\alpha_0$ may be the maximum flip angle and the ending flip angle $\alpha_{N-1}$ may be the minimum flip angle in the phase, vice versa. The minimum flip angle may be within a range to reduce the artifact, while the maximum flip angle may be within a range to reduce SAR.

After a group of optimal or suitable flip angles is determined, the MRI system may perform imaging. The MRI system may generate refocusing RF pulses in step 1006 according to the group of optimal or suitable flip angles. In step 1007, one or more echo trains may be detected. In some embodiments, the ETL may be either fixed or variable. In some embodiments, the ETL may be adaptive. One or more echo trains may be utilized to fill a k-space. The echoes to fill the central lines of the k-space may be selected on a basis of image contrast. In some embodiments, any phase (e.g., a steady state phase of an echo train) may be utilized to fill the central lines of the k-space. It should be noted that any number of phases may be utilized to fill the central lines of the k-space, regardless of whether they are continuous or discrete. It should be further noted that any number of echoes (e.g., two echoes with the maximum difference) may be utilized to fill the central lines of the k-space. In step 1008, one or more images of one or more selected portions of interest may be produced.

It should be understood by persons having ordinary skills in the art that the present disclosure may be practiced according to various variations and modifications under the teachings of the present disclosure. The variations and modifications may be practiced without those specific details described in the flowchart. However, those variations and modifications do not depart from the spirit of the present disclosure. For example, step 1001 and step 1002 may be performed sequentially regardless of the order, or may be performed concurrently. Furthermore, step 1001 and step 1002 may be merged into one step, and step 1006 and step 1007 may be merged into one step.

In some embodiments of the present disclosure, the systems, units, modules, engines, or blocks may be modified or may operate automatically and/or semi-automatically. In the exemplary embodiments of manual mode, the operations or processes may be executed with the same spirits of the above embodiments. In the exemplary embodiments of automatic and/or semi-automatic mode, the operations that may be performed automatically or semi-automatically includes processes, information selection or maintenance, etc. for a flip angle determination. Exemplary processes include self-initialization, automatically selecting parameters, automatically calculating a flip angle schedule, self-calculating signal schedule, automatically assessing the calculated flip angle schedule, automatically determining and saving desired information, or the like, or any combination thereof. Exemplary information includes programs, software, algorithms, functions, parameters, data, text, number, images, or the like, or any combination. The establishment, maintenance, renewal, or deletion of the processes and/or information that may be operated automatically or semi-automatically may be preloaded by an external resource, e.g., an operator, or may be acquired by self-learning or trial-and-error based on prior operations performed by one or more MRI systems, or based on a specific imaging process, or other means. In some embodiments, the system may be switched among a manual mode, an automatic mode, and a semi-automatic mode. These three modes may provide different choices to a user and allow the user to participate in the imaging process in a proper level. Merely by way of example, a user with a first level of access privilege may be allowed to provide a set of information on the basis of which the MRI system selects a flip angle schedule from a library of flip angle schedules pre-loaded in the MRI system. As another example, a user with a second level of access privilege may request a personalized determination of a suitable flip angle schedule for a specific imaging. As a further example, a user with a third level of access privilege may update a library of flip angle schedules stored in or accessible by the MRI system.

In some embodiments of the present disclosure, for one kind of subject of interest (e.g., a tissue, a body, etc.), a library of predetermined patterns or flip angle schedules may be saved in the magnet resonance imaging system from which a user may select for a specific imaging process. Exemplary subjects include brain, brain-stem, five sense organs, neck, spinal column, heart, breast, muscle, skeleton, joint, soft tissue, liver, pancreas, bile ducts, or the like, or any combination thereof. These predetermined patterns may be pre-loaded by an external operator, or by self-learning during prior imaging processes. The predetermined patterns may carry the information including programs, software, algorithms, functions, parameters, data, text, number, images, or the like, or any combination of one specific subject. Exemplary parameters may include image contrast and/or ratio, subject of interest, slice thickness, imaging type (T1 weighted imaging, T2 weighted imaging or proton density weighted imaging), T1, T2, spin echo type (spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), number of phases, number of excitations (NEX), inversion time, bandwidth (e.g., RF receiver bandwidth, RF transmitter bandwidth, etc.), a function for describing the flip angle schedule or a portion thereof (e.g., a phase of an entire flip angle schedule), a reference signal schedule, or the like, or any combination thereof. The function(s) may include the Bloch equation, the EPG algorithm, a polynomial, a linear function, a trigonometric function, an anti-trigonometric function, an exponential function, a power function, a logarithmic function, or the like, or any combination thereof. When same or similar tissues from the same or a different body are to be imaged, the predetermined modes may be offered and thus the process for determining a flip angle schedule may be skipped. The entire or part of a predetermined pattern may be applied to a new imaging process. For example, in some embodiments, all the information, e.g., programs, software, algorithms, functions, parameters, data, text, number, images, or the like, or any combination of a predetermined pattern may be used in a specific imaging process. In some embodiments, some parts of the information, e.g., programs, software, algorithms, functions, parameters, data, text, number, images, or the like, or any combination of a predetermined pattern may be used in a specific imaging process.

In some embodiments of the present disclosure, preferred parameter(s) or information may be determined based on a reference signal schedule, the quality of an MR image, or the like, or any combination thereof. For example, when a flip angle schedule whose signal evolution are assessed to be suitable or satisfactory based on the reference signal schedule or a desired image quality, one or more parameters or information including, e.g., the programs, software, algorithms, functions, etc. used in determining the flip angle schedule may be classified as preferred ones. The preferred parameter(s) or information may be saved as a reference for future use. As another example, a flip angle schedule may lead to a satisfactory signal evolution (e.g., signal evolution calculated based on a relationship between the flip angle schedule and the signal evolution) based on an assessment with reference to a reference signal schedule, actual MR images of unsatisfactory quality, one or more parameters or information including, e.g., the programs, software, algorithms, functions, etc. used in determining the flip angle schedule may be classified as non-preferred or may be deleted or removed from, or not saved in the library.

Figure 11:
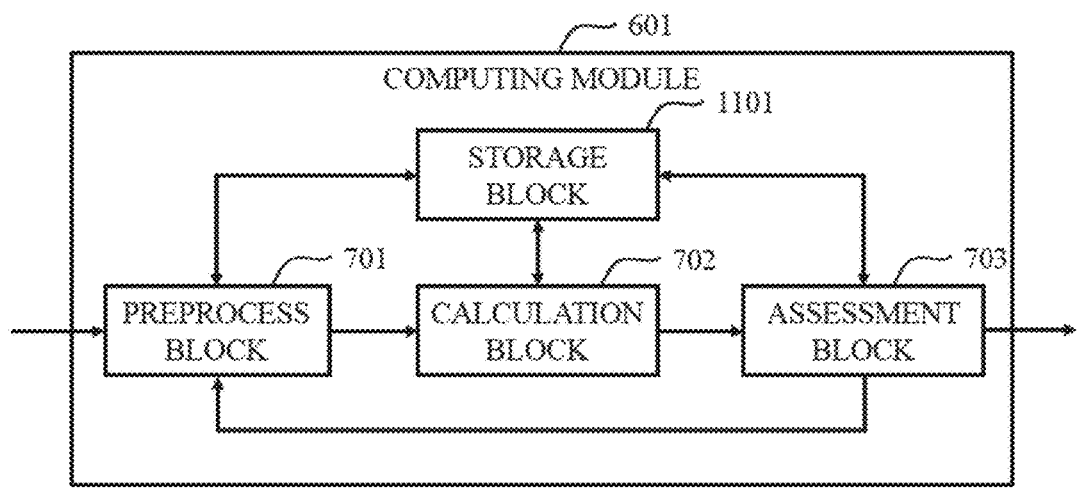
FIG. 11 is a block diagram depicting a computing module according to some embodiments of the present disclosure.

FIG. 11 is a block diagram illustrating a computing module 601 according to some embodiments of the present disclosure. Note that the construction or assembly of the computing module may have some other variations, FIG. 11 is provided for illustration purposes. With reference to FIG. 11, the computing module 601 may include a preprocess block 701, a calculation block 702, an assessment block 703 and a storage block 1101. The preprocess block 701 may be configured or used to execute some operations such as system initiation and/or parameter presetting. The calculation block 702 may be configured or used to calculate some information based on the initial or preset information from the preprocess block 701. The information may include programs, software, algorithms, data, text, number, images, voice, or the like, or any combination thereof. The functions for flip angle calculation may include the Bloch equation, the EPG algorithm, a polynomial, a linear function, a trigonometric function, an anti-trigonometric function, an exponential function, a power function, a logarithmic function, or the like, or any combination thereof. Exemplary algorithms may include recursion, a bisection method, an exhaustive search (or brute-force search), a greedy algorithm, a divide and conquer algorithm, a dynamic programming method, an iterative method, a branch-and-bound algorithm, a backtracking algorithm, or the like, or any combination thereof. The algorithms may be executed on a software or a program such as a general Math software. Exemplary software or program may include Matlab, Maple, Mathematica, MathCad, and/or numpy/scipy/sympy based on python and so on. The assessment block 703 may be configured or used to determine if the information from the calculation block 702 satisfies some requirements, rules, criteria, thresholds or standards Note that the requirements, criteria, thresholds or standards may be different in different phases of a flip angle schedule, as described elsewhere in the present disclosure. The storage block 1101 may be configured or used to store, e.g., preferred parameters or information as described elsewhere in the present disclosure. In some embodiments, the assessment whether one or more parameters or information is preferred may be performed by the assessment block 703. Exemplary preferred parameters or information stored in the storage block 1101 may include programs, software, algorithms, data, text, number, images and other information from the preprocessing block 701, the calculation block 702, and/or assessment block. During an MR imaging process, the preferred parameters or information in the storage block 1101 may be automatically or semi-automatically imported to other blocks in the computing module 601 if the computing module 601 is set in automatic or semi-automatic mode. The automatic or semi-automatic mode may relieve the burden of the computing module 601 by employing preferred parameters or information acquired from prior computing or imaging processes. Preferred parameters or information may be updated or optimized periodically or aperiodically.

As shown in FIG. 11, the preprocess block 701 may be configured or used to preset some factors or parameters relative to flip angle calculation. The factors or the parameters may include image contrast and/or ratio, subject of interest, slice thickness, imaging type (e.g., T1 weighted imaging, T2 weighted imaging or proton density weighted imaging), T1, T2, a spin echo type (e.g., spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), or the like, or any combination thereof.

The calculation block 702 may include or be implemented on a device to calculate a flip angle sequence by different functions and/or algorithms based on the initial information preset in the preprocess block 701. Exemplary functions or algorithms may include the Bloch equation, the EPG algorithm, a polynomial, a linear function, a trigonometric function, an anti-trigonometric function, an exponential function, a power function, a logarithmic function, recursion, a bisection method, an exhaustive search (or brute-force search), a greedy algorithm, a divide and conquer algorithm, a dynamic programming method, an iterative method, a branch-and-bound algorithm, a backtracking algorithm, or the like, or any combination thereof. The functions or algorithms may be executed on a software or a program such as general Math software. Exemplary software or program may include Matlab, Maple, Mathematica, MathCad, and/or numpy/scipy/sympy based on python and so on.

The assessment block 703 may assess if the flip angles calculated by the calculating block 702 satisfy a requirement, criterion, threshold, or standard. If the flip angles satisfy the requirement, criterion, threshold, or standard, it may be stored or output for further process or future use. If the flip angles do not satisfy the requirement, criterion, threshold, or standard, the MRI system may return to the preprocess block 701 and/or calculating block 702, and iterate the operations until a requirement, criterion, threshold, or standard is satisfied determined by, e.g., the assessment block 703. It should be noted that the requirements, criteria, thresholds or standards may be different in different phases of a flip angle schedule, as described elsewhere in the present disclosure.

It should also be noted that in this embodiment, the preprocess block 701, the calculation 702, and the assessment block 703 may import and utilize preferred parameter(s) or information stored in the storage block 1101 if the computing module 601 is set on automatic or semi-automatic mode.

If a new subject is imaged in the MRI system, the flip angle calculation may be conducted according to the flowchart of FIGS. 8-10. During the flip angle calculation in FIGS. 8-10, the initial condition or information that generates suitable results may be stored in the storage block 1101. For example, the initial condition or information may include a preferred initial flip angle, a preferred reference signal schedule, a preferred algorithm, a preferred norm, a preferred ETL, a preferred flip angle schedule, a preferred function for calculating a flip angle schedule, or the like, or any combination thereof. Such preferred initial information may be stored in the storage block 1101. When a same or similar subject is to be imaged, the computing module 601 may optionally refer to the preferred parameter(s) or information.

It should be noted that these embodiment are only exemplary and not intended to be limiting, and further embodiments also include some variations that will become apparent to those of ordinary skill in the art upon consulting the present disclosure. For example, the assembly and/or function of computing module 601 may be varied or changed. In some embodiments, the storage block 1101 may be put outside the computing module 601, or integrated into the storage module 603. However, those variations or modifications do not depart from the scope of the present disclosure.

Figure 12:
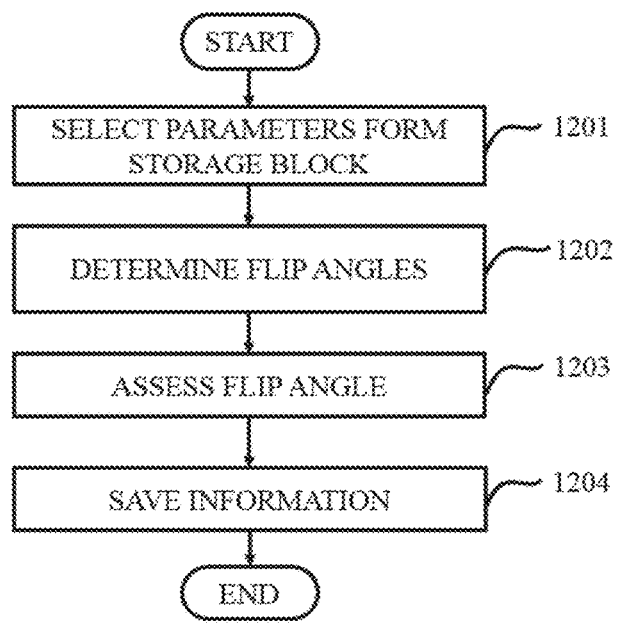
FIG. 12 is a flowchart illustrating a process for the determination of a flip angle schedule according to some embodiments of the present disclosure.

FIG. 12 is a flowchart illustrating a process for flip angles determination according to some embodiments of the present disclosure. In step 1201, parameters for the calculation of a flip angle schedule may be set or processed. Before setting or processing the parameters, the MRI system may assess whether imaging has been performed on a same or similar subject in the system or records regarding the same or a similar subject are available. When the system decides that imaging has been performed on the same or a similar subject, a predetermined pattern relating to the prior imaging or records may be selected. In some embodiments of the present disclosure, the parameters may include image contrast and/or ratio, a subject of interest, slice thickness, an imaging type (e.g., T1 weighted imaging, T2 weighted imaging, proton density weighted imaging, etc.), T1, T2, a spin echo type (e.g., spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), a function for describing the flip angle schedule or a portion thereof (e.g., a phase of an entire flip angle schedule), or the like, or any combination thereof.

In some embodiments, an echo train may be divided into one or more phases. See, for example, relevant description in connection with FIG. 8. In some embodiments of the present disclosure, each phase of an echo train may have its own condition including initial parameters (e.g., starting flip angle, ending flip angle, etc.), a function (e.g., a function for calculating the flip angle(s) of the phase, etc.), an algorithm (e.g., an algorithm for flip angle optimization), a reference signal schedule (e.g., a continuous signal evolution, a group of discrete reference signals, a target root mean square (RMS) in a phase, a mean value, or the like, or any combination thereof), a signal evolution selection criterion, or the like, or any combination thereof. In some embodiments, each echo train may have two or more phases. The conditions of different phases may be the same or different. In some embodiments, the impact of the flip angles of different phases on the resultant MR signals may be the same or different. For instance, an MR signal corresponding to an echo is obtained based on a refocusing RF pulse of a flip angle belonging to a specific phase, and the flip angle of the specific phase may have more impact on the resultant MR signals than the flip angles of another phase. The flip angles of the different phases may be processed sequentially, randomly, simultaneously, etc. In some embodiments, the phase(s) with higher impact may be seen as priority phase(s). The non-priority phase(s) may be subject to less or no restrictions and may be adjusted as needed to ensure that the priority phase(s) attain(s) its or their corresponding condition.

It should be noted that the above embodiments are for illustration purposes and not intended to limit the scope of the present disclosure. The embodiments may be variable, changeable, or adjustable based on the spirits of the present disclosure. For example, flip angle calculation in different phases may be based on a same function or different functions chosen from, for example, the Bloch equation, the EPG algorithm, a polynomial, a linear function, a trigonometric function, an anti-trigonometric function, an exponential function, a power function, a logarithmic function, or the like, or any combination thereof. As another example, the phases and/or the condition or parameters of phases may be given different weight. However, those variations and modifications do not depart from the scope of the present disclosure.

One or more flip angles of the refocusing RF signals may be determined in step 1202. In some embodiments of the present disclosure, the flip angles may be determined based on, e.g. functions according to preferred functions as described elsewhere in the present disclosure. See, e.g., relevant description regarding FIG. 10. The initial conditions including, e.g., the starting flip angle, the ending flip angle in a phase, a group of flip angles may be determined. The MRI system may assess whether a group of desired flip angles are achieved. The assessment may be based on a comparison between a signal evolution and a favorable reference signal schedule, while the signals evolution may be determined on the basis of the flip angles determined in step 1203. In some embodiments, the assessment may be based on whether one or more resultant signals of a resultant evolution satisfy a requirement, criterion, threshold, or standard. In some embodiments, the assessment may be based on whether a section (e.g., a phase or a portion) of a resultant evolution satisfy a requirement, criterion, threshold, or standard. In some embodiments, the assessment may be based on a comparison among several resultant signal evolutions. In some embodiments, the assessment may be based on a comparison between the resultant signal evolutions with a reference signal schedule (e.g., a preferred equation). See relevant disclosure elsewhere in the present disclosure regarding the assessment. In step 1204, the parameter(s) or information used to determine a group of optimized flip angles in FIG. 12 may be saved to update the storage block 1101. The parameter(s) or information that need to be stored may include programs, software, algorithms, data, text, number, images, voice, or the like, or any combination thereof.

It should be noted that the flowchart described above is provided for the purposes of illustration, and not intended to limit the scope the present disclosure. For persons having ordinary skills in the art, a certain amount of variations and modifications may be reduced under guidance of the present disclosure. For example, the computing module 601 may be chosen either under an automatic mode, a semi-automatic mode, or a manual mode as described in connection with FIGS. 8-10.

Figure 13:
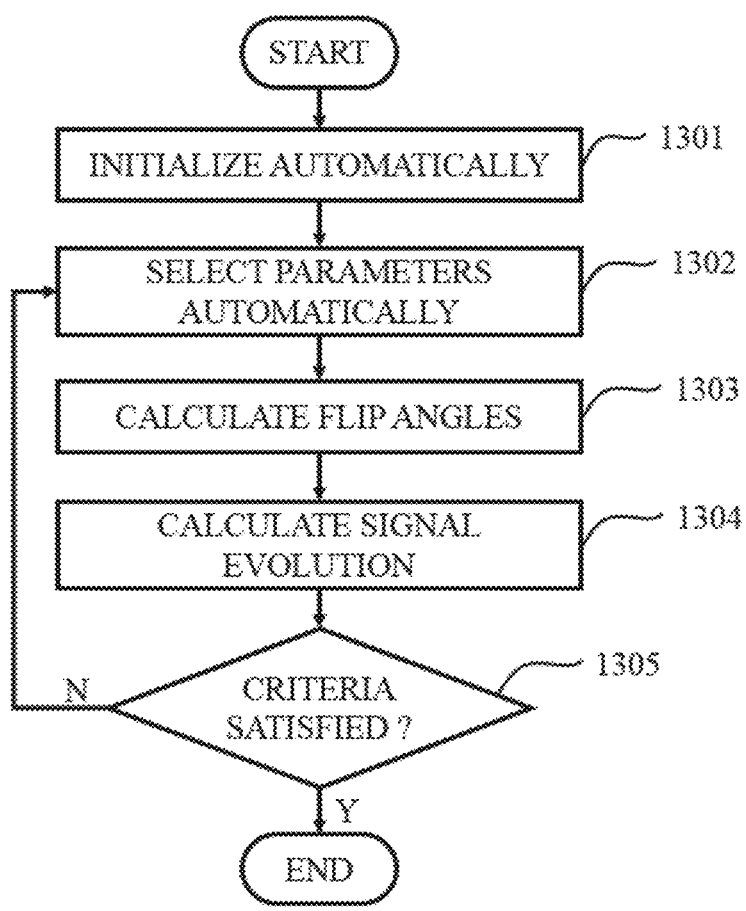
FIG. 13 is a flowchart illustrating a process for the determination of a flip angle schedule according to some embodiments of the present disclosure.

FIG. 13 is a flowchart illustrating an exemplary process for determining a flip angle schedule according to some embodiments of the present disclosure. In step 1301, initiation may be performed automatically or semi-automatically. In some embodiments of the present disclosure, the initiation may include setting an initial condition including, e.g., one or more parameters. The parameters may include image contrast and/or ratio, a subject of interest, slice thickness, an imaging type (e.g., T1 weighted imaging, T2 weighted imaging, proton density weighted imaging, etc.), T1, T2, a spin echo type (spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), a function for describing the flip angle schedule or a portion thereof (e.g., a phase of an entire flip angle schedule), a reference signal schedule, or the like, or any combination thereof. The function(s) may include the Bloch equation, the EPG algorithm, a polynomial, a linear function, a trigonometric function, an anti-trigonometric function, an exponential function, a power function, a logarithmic function, or the like, or any combination thereof.

The MRI system may perform a parameters selection in step 1302 according to the preferred parameters stored in, e.g., the storage block 1101. The parameters in step 1302 may be different from the parameters described in step 1301. In some embodiments of the present disclosure, the parameters may include, without limitation to, the number of phases, a starting flip angle, an ending flip angle, a flip angle calculation function, arguments, a reference signal schedule, or the like, or any combination thereof. The number of phases may be utilized to indicate the how an echo train is divided. In some embodiments, for two adjoining phases (one preceding the other), the ending flip angle of the preceding phase may be utilized as the starting flip angle of the phase following the preceding phase. The functions for flip angle calculation may include the Bloch equation, the EPG algorithm, a polynomial, a linear function, a trigonometric function, an anti-trigonometric function, an exponential function, a power function, a logarithmic function, or the like, or any combination thereof.

In step 1303, the calculation of flip angles may be performed. A group of flip angles may be generated in step 1303. In step 1304, a signal evolution may be calculated based on the flip angles calculated in step 1303 according to, e.g., the EPG algorithm and/or the Bloch equation. In step 1305, an assessment of a flip angle schedule may be made based on a resultant signal evolution corresponding to the calculated flip angle schedule, as described elsewhere in the present disclosure. If the criteria is met in step 1305, the flip angle calculation may be terminated. Otherwise, a new group of flip angles may be calculated by repeating steps 1302-1304. The number of iterations may be either fixed or variable. In some instances, the number of iterations may be adaptive. The new group of flip angles may be calculated by adjusting parameters including, e.g., the starting flip angle $\alpha_0$, the ending flip angle $\alpha_{N-1}$, and the characteristic parameter P of each phase as described in Equation 1 and Equation 2. The MRI system may adjust any one of the three parameters, or any two of the three parameters, or all three parameters to calculate a new group of flip angles. The parameters may be adjusted in step 1502. Merely by way of example, parameters including, e.g., the starting flip angle, the ending flip angle, the characteristic parameter P, may be adjusted using an algorithm. Exemplary algorithms may include recursion, a bisection method, an exhaustive search (or brute-force search), a greedy algorithm, a divide and conquer algorithm, a dynamic programming method, an iterative method, a branch-and-bound algorithm, a backtracking algorithm, or the like, or any combination thereof.

It should be noted that the flowchart described above is provided for the purposes of illustration, and not intended to limit the scope the present disclosure. For persons having ordinary skills in the art, a certain amount of variations and modifications may be reduced under guidance of the present disclosure.

Figure 14:
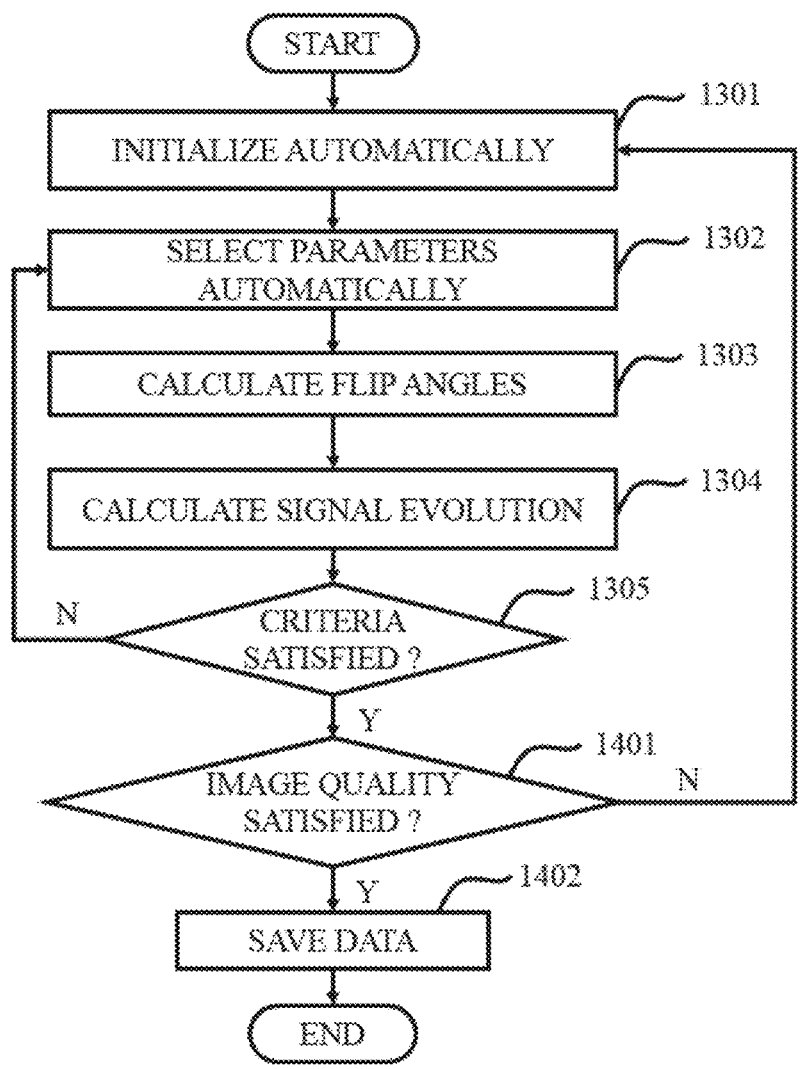
FIG. 14 is a flowchart illustrating a process for MRI according to some embodiments of the present disclosure.

FIG. 14 illustrates a process for MR imaging according to some embodiments of the present disclosure. A flip angle schedule may be determined based on desired image quality. Steps 1301-1305 are the same as described above in connection with FIG. 13.

A group of optimized or suitable flip angles that satisfy the criteria may be used for generating refocusing RF pulses and MR images. In step 1401, the image quality may be assessed. The image quality may include image contrast, image resolution, mean squared error (MSE), signal to noise rate (SNR), artifacts, the like, or any combination thereof. If the images produced by a group of optimized flip angles satisfies a quality requirement, rule, criterion, threshold, or a standard, the corresponding group of optimized flip angles and the parameter(s) or information used to determine the flip angles may be saved in, e.g., the storage block 1101 in step 1402. If the images do not satisfy the quality requirement, rule, criterion, threshold, or standard, the parameter(s) or information used to determine the flip angles may be adjusted to determine a new group of optimized flip angles until an MR image of a suitable quality is obtained.

Figure 15A:
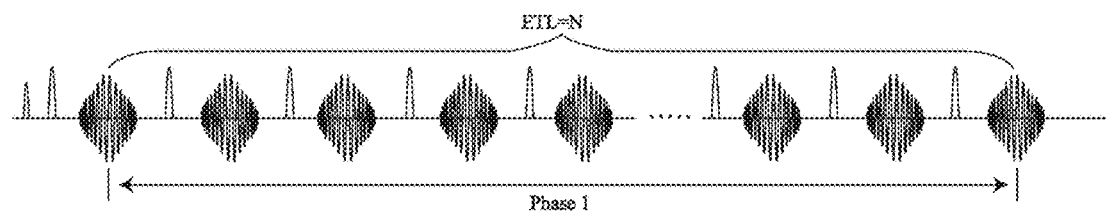
FIGS. 15A-15C illustrate exemplary echo trains according to some embodiments of the present disclosure.
Figure 15B:
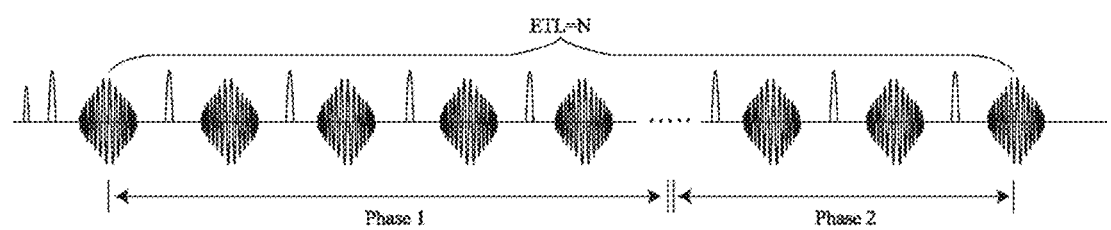
Figure 15C:
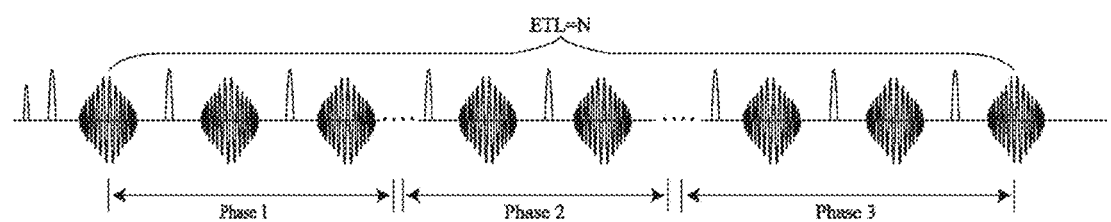

FIGS. 15A-15C illustrate three exemplary echo trains according to some embodiments of the present disclosure. The echo train illustrated in FIG. 15A has one phase in total. In some embodiments, the flip angle schedule may be described using Equation 1 or Equation 2. Merely by way of example, in connection with Equation 1 and Equation 2, the initial value of the characteristic parameter P may be set to N that is the echo train length (ETL). The initial condition for the starting flip angle and the ending flip angle may be assigned randomly, or assigned with desired values (e.g., desired maximum and minimum flips angles), respectively. Once the characteristic parameter P, the starting flip angle and the ending flip angle are specified, the calculation of the remaining flip angles may be performed until an optimized group of flip angles is achieved. The optimized group of flip angles may be calculated according to the process described elsewhere in the present disclosure. See, e.g., FIGS. 8-10 and 12-14 and the descriptions thereof. The exemplary echo train illustrated in FIG. 15A may be used for generating T1 weighted MR images.

Referring to FIG. 15B, the echo train is divided into 2 phases. In some embodiments, each phase of the flip angle schedule may be described using equation 1 and equation 2. Merely by way of example, in connection with equation 1 and equation 2, the initial value of the characteristic parameter P of phase 1 may be set to N/3, while the initial value of the characteristic parameter P of phase 2 may be set to N. The number of echoes in phase 1 may be set to N/2, while the number of echoes in phase 2 may be set to N/2 as well. The starting flip angle and the ending flip angle of each phase may be assigned randomly, or assigned with desired values (e.g., desired maximum and minimum flips angles), respectively. A group of optimized flip angles may be calculated according to the process described elsewhere in the present disclosure. See, e.g., FIGS. 8-10 and 12-14 and the descriptions thereof. The exemplary echo train illustrated in FIG. 15B may be used for generating proton density weighted MR images.

Referring to FIG. 15C, the whole echo train may be divided into three phases. In some embodiments, each phase of the flip angle schedule may be described using equation 1 and equation 2. Merely by way of example, in connection with equation 1 and equation 2, the initial value of the characteristic P of phase 1 may be set to N/3, and the initial value of the characteristic P of phase 2 and the initial value of the characteristic P of phase 3 may be set to N. The number of echoes in phase 1 may be set to N/10, the number of echoes in phase 2 may be set to N/2.5, and the number of echoes in phase 3 may be set to N/2. The initial condition for the starting flip angle and the ending flip angle of each phase may be assigned randomly, or assigned with desired values (e.g., desired maximum and minimum flips angles), respectively. An optimized group of flip angles may be calculated based on according to the process described elsewhere in the present disclosure. See, e.g., FIGS. 8-10 and 12-14 and the descriptions thereof. The exemplary echo train illustrated in FIG. 15C may be used for generating T2 weighted MR images.

Merely by way of example, concerning the relaxation time of a particular tissue, for example, the gray matter in 1.5 T filed (T1=960 ms, T2=100 ms), the whole echo train may be divided into three phases. The reference signal schedule may include at least one of the following features: (a) in phase 2 the signal is in pseudo-steady state and has the possible largest intensity; (b) on the basis of (a), in phase 3 the signals reach the largest intensity at the end of the signal; (c) no requirements are set for phase 1. The initial value of the characteristic P of phase 1 may be set to ETL/10, the initial value of the characteristic P of phase 2 and the initial value of the characteristic phase 3 may be set to ETL. To calculate the optimized group of flip angles, the initial condition for 4 flip angles may be set randomly or set to desired values. Merely by way of example, the ending flip angle of phase 1 and the starting flip angle of phase 2 may be the same; the ending flip angle of phase 2 and the starting flip angle of phase 3 may be the same. An optimized group of flip angles may be calculated based on according to the process described elsewhere in the present disclosure. See, e.g., FIGS. 8-10 and 12-14 and the descriptions thereof.

Figure 16A:
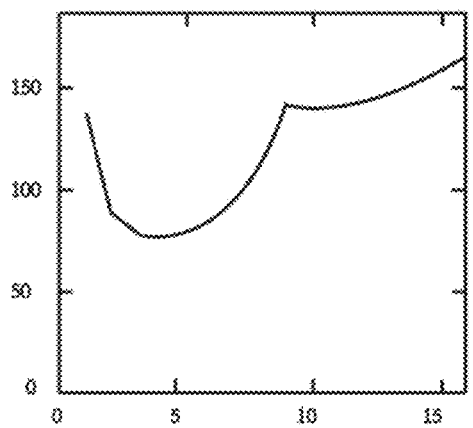
FIGS. 16A and 16B illustrate a flip angle schedule and corresponding signal evolutions according to some embodiments of the present disclosure.
Figure 16B:
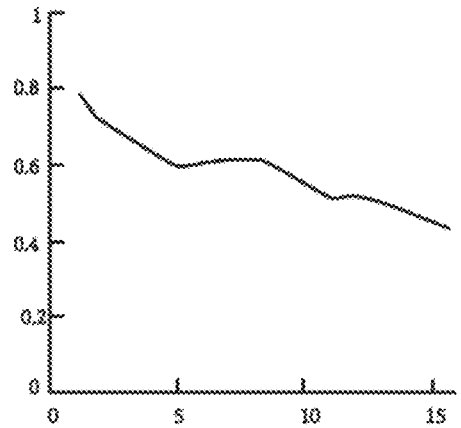

FIGS. 16A and 16B illustrate a flip angle schedule and a signal evolution according to some embodiments of the present disclosure. FIG. 16A illustrates the flip angle schedule, while FIG. 16B illustrates the corresponding signal evolution obtained based on the flip angle schedule in FIG. 16A. The flip angles are calculated according to the embodiment illustrated in FIG. 15C, and ETL is set to 16. As shown in FIG. 16B, the signal intensity in the steady state (between echo 5 and echo 10) may reach 0.65.

Figure 17A:
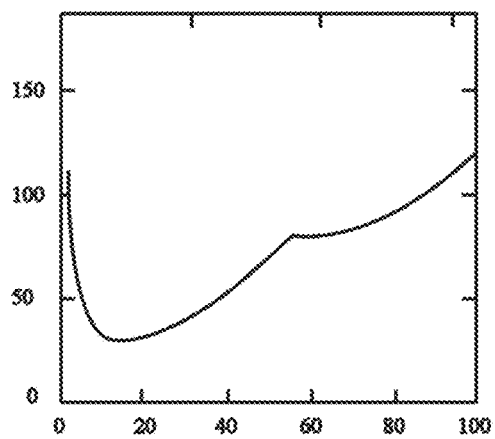
FIGS. 17A and 17B illustrate a flip angle schedule and corresponding signal evolutions according to some embodiments of the present disclosure.
Figure 17B:
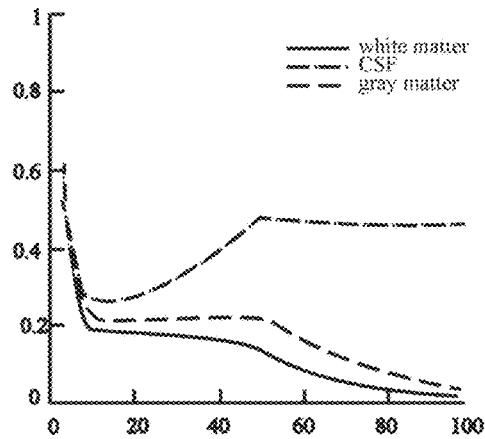

FIGS. 17A and 17B illustrate a flip angle schedule and signal evolutions according to some embodiments of the present disclosure. FIG. 17A illustrates the flip angle schedule, while FIG. 17B illustrates three exemplary signal evolutions in respect to gray matter, white matter, and CSF calculated based on the flip angle schedule. The flip angles illustrated in FIG. 17A correspond to the embodiment illustrated in FIG. 15C, and ETL is set to 100. As specified in FIG. 17B, the signal intensity of gray matter may reach 0.22 in the steady state.

EXAMPLES

The following examples are provided for illustration purposes, and not intended to limit the scope of the present disclosure.

Figure 18A:
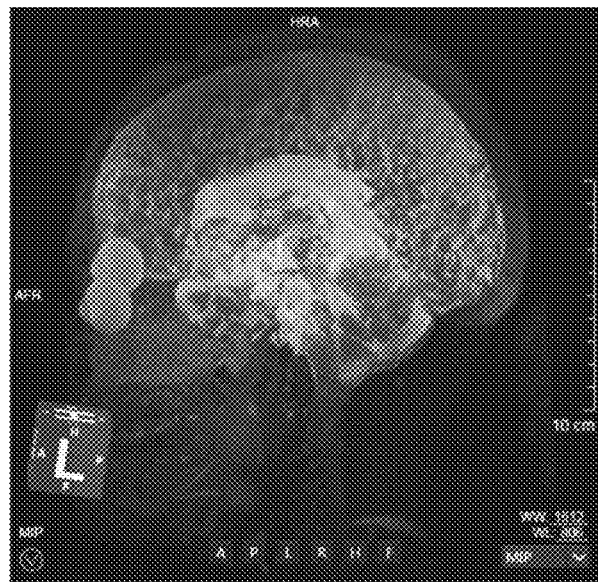
FIGS. 18A-18D show example MR images obtained using a flip angle schedule including variable flip angles according to some embodiments of the present disclosure.
Figure 18B:
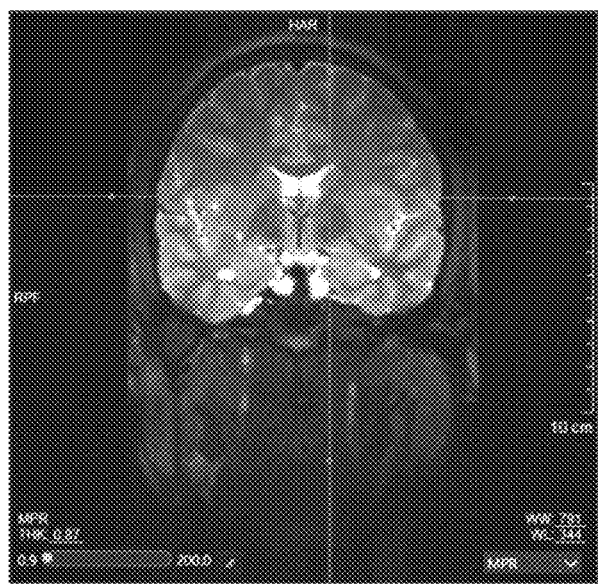
Figure 18C:
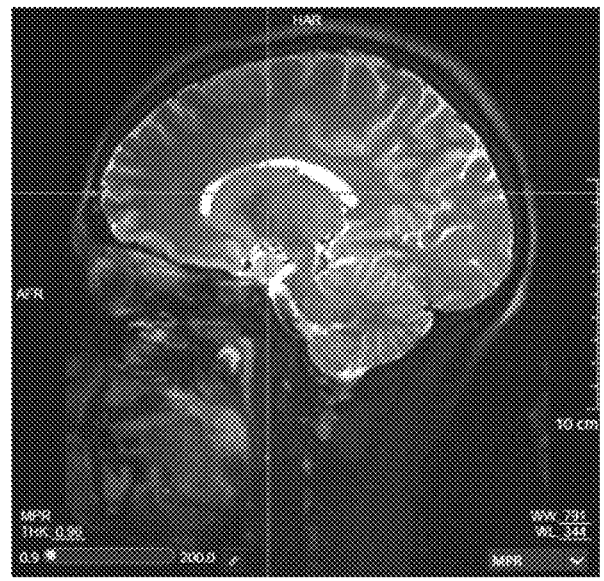
Figure 18D:
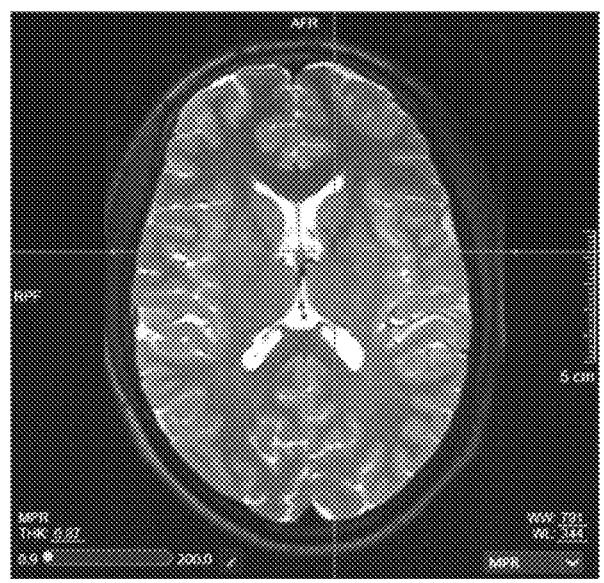

FIGS. 18A-18D show example MR images obtained using a flip angle schedule including variable flip angles according to some embodiments of the present disclosure. The length of the echo train was set to 220, and the echo train was divided into three phases. The number of echoes in phase 1, phase 2, phase 2 were 28, 88 and 104, respectively. The initial value of the characteristic P of phase 1, phase 2, and phase 3 were 22, 220 and 220, respectively. No restrictions were specified regarding the signals of phase 1 and phase 3. The restrictions regarding signals in phase 2 were that the signals of phase 2 varied smoothly and their intensities were as strong as practically possible. According to the above restrictions, a group of optimized flip angles were determined and used to build several sets of 3D brain images shown in FIGS. 18A-18D. The resolution was 0.9 mm×0.9 mm×0.9 mm. The 3D brain images may also be reconstructed in any plane or direction so that tiny lesions may be located accurately. FIG. 18A is an exemplary reconstruction of the 3D brain images with maximum intensity projection (MIP) FIGS. 18B-18D are exemplary reconstructions of the 3D brain images in coronal view, sagittal view, and transversal view, respectively. Various details of the brain were visible in the figures.

It should be noted that the above description of the three embodiments are provided for a purpose of comprehending the present disclosure, not intended to limit the scope of the present disclosure. For persons having ordinary skills in the art, various variations and modification may be conducted in the light of the present disclosure. However, the variations and the modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHW, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

What is claimed is:

1. A magnetic resonance imaging (MRI) system comprising: an MRI scanner, a control unit, and a processing unit, the processing unit performing operations comprising:
    a) selecting an initial condition relating to a first phase of an echo train, the initial condition including initial values of a first flip angle, a last flip angle, and a first characteristic parameter;
    b) providing a first function corresponding to the first phase echo train, the first function relating to at least one of the first flip angle, the last flip angle, or the first characteristic parameter;
    c) calculating, based on the first function, one or more flip angles corresponding to one or more spin echoes of the first phase;
    d) assessing the one or more flip angles of the first phase according to a first criterion; and
    e) if the first criterion is not satisfied,
        revising the first function by adjusting at least one of the first flip angle, the last flip angle, or the first characteristic parameter, and repeating (c) and (d);
    wherein the first function provides a flip angle schedule corresponding to the first phase of the echo train for MRI, and
    the control unit controlling the MRI scanner according to the flip angle schedule,
    wherein the first function includes:

$$\alpha_n = \alpha_M + (|\alpha_0 - \alpha_{N-1}|) \cdot \frac{e^{\left(\frac{(M-n)^2}{P^2}\right)} - 1}{e^{\left(\frac{(N-1)^2}{P^2}\right)} - 1},$$

where $\alpha_0$ is the first flip angle of the first phase, $\alpha_{N-1}$ is the last flip angle of the first phase, N is a number of echoes in the first phase, P is the characteristic parameter of the first phase, $\alpha_n$ is the one or more flip angles of the first phase, n=0, 1, ..., N−1;
where M=0 if $\alpha_{N-1} \geq \alpha_0$, or M=N−1 if $\alpha_0 > \alpha_{N-1}$.

2. The MRI system of claim 1, the assessing of the one or more flip angles of the first phase comprising:
    calculating, based on the one or more flip angles of the first phase, a first signal evolution; and
    evaluating the first signal evolution according to the first criterion.

3. The MRI system of claim 2,
    the first criterion comprising a first threshold, and
    the assessing of the one or more flip angles of the first phase comprising determining whether a maximum signal in the first signal evolution equals to or exceeds the first threshold.

4. The MRI system of claim 1, the processing unit further performing:
    (f) providing a reference signal schedule corresponding to the first phase, the reference signal schedule comprising one or more reference signals corresponding to the one or more spin echoes of the first phase.

5. The MRI system of claim 4, the assessing of the one or more flip angles of the first phase comprising:
    calculating, based on the one or more flip angles of the first phase, a first signal evolution; and
    comparing the first signal evolution with the reference signal schedule.

6. The MRI system of claim 4, the reference signal schedule relating to T1 or T2 of a tissue to be imaged using the flip angle schedule corresponding to the first phase of the echo train for magnetic resonance imaging.

7. The MRI system of claim 1, the processing unit further performing:
    g) selecting a second initial condition relating to a second phase of the echo train, the second initial condition including initial values of a third flip angle, a fourth flip angle, and a second characteristic parameter;
    h) providing a second function corresponding to the second phase, the second function relating to at least one of the third flip angle, the fourth flip angle, or the second characteristic parameter;
    i) calculating; based on the second function, one or more flip angles corresponding to one or more spin echoes of the second phase;
    j) assessing the one or more flip angles of the second phase according to a second criterion; and k) if the second criterion is not satisfied,
revising the second function by adjusting at least one of the third flip angle; the fourth flip angle, or the second characteristic parameter, and repeating (i) and (j);
wherein the second function provides a flip angle schedule corresponding to the second phase of the echo train for magnetic resonance imaging.

8. The MRI system of claim 7; the third flip angle being the same as the initial value of the last flip angle or the adjusted last flip angle.

9. A method comprising:
a) selecting an initial condition relating to a first phase of an echo train, the initial condition including initial values of a first flip angle, a last flip angle, and a first characteristic parameter;
b) providing a first function corresponding to the first phase of the echo train, the first function relating to at least one of the first flip angle, the last flip angle, or the first characteristic parameter;
c) calculating, based on the first function, one or more flip angles corresponding to one or more spin echoes of the first phase;
d) assessing the one or more flip angles of the first phase according to a first criterion; and
e) if the first criterion is not satisfied,
revising the first function by adjusting at least one of the first flip angle, the last lip angle, or the first characteristic parameter, and repeating (c) and (d);
wherein the first function provides a flip angle schedule corresponding to the first phase of the echo train for MRI,
wherein the first function includes:

$$\alpha_n = \alpha_M + (|\alpha_0 - \alpha_{N-1}|) \cdot \frac{e^{\left(\frac{(M-n)^2}{P^2}\right)} - 1}{e^{\left(\frac{(N-1)^2}{P^2}\right)} - 1},$$

where $\alpha_0$ is the first flip angle of the first phase, $\alpha_{N-1}$ is the last flip angle of the first phase, N is a number of echoes in the first phase, P is the characteristic parameter of the first phase, $\alpha_n$ is the one or more flip angles of the first phase, n=0, 1, . . . , N−1;
where M=0 if $\alpha_{N-1} \geq \alpha_0$, or M=N−1 if $\alpha_0 > \alpha_{N-1}$.

10. The method of claim 9, the assessing of the one or more flip angles of the first phase comprising:
calculating, based on the one or more flip angles of the first phase, a first signal evolution; and
evaluating the first signal evolution according to the first criterion.

11. The method of claim 10, the calculating of the first signal evolution comprising using the Bloch equation or the EPG algorithm.

12. The method of claim 10,
the first criterion comprising a first threshold, and
the assessing of the one or more flip angles of the first phase comprising determining whether a maximum signal in the first signal evolution equals to or exceeds a first threshold.

13. The method of claim 9 further comprising:
(f) providing a reference signal schedule corresponding to the first phase, the reference signal schedule comprising one or more reference signals corresponding to the one or more spin echoes of the first phase.

14. The method of claim 13, the assessing of the one or more flip angles of the first phase comprising:
calculating, based on the one or more flip angles of the first phase, a first signal evolution; and
comparing the first signal evolution with the reference signal schedule.

15. The method of claim 9, the magnetic resonance imaging comprising T1 weighted imaging, T2 weighted imaging, or proton density weighted imaging.

16. The method of claim 9, the adjusting of the at least one of the first flip angle, the last flip angle, or the first characteristic parameter comprising using recursion, a bisection method, an exhaustive search, a greedy algorithm, a divide and conquer algorithm, a dynamic programming method, an iterative method, a branch-and-bound algorithm, or a backtracking algorithm.

17. The method of claim 9 further comprising:
g) selecting a second initial condition including initial values of a third flip angle, a fourth flip angle, and a second characteristic parameter;
h) providing a second function corresponding to a second phase, the second function relating to the third flip angle, the fourth flip angle, and the second characteristic parameter;
i) calculating, based on the second function, one or more flip angles corresponding to one or more spin echoes of the second phase;
j) assessing the one or more flip angles of the second phase according to a second criterion; and
k) if the second criterion is not satisfied,
revising the second function by adjusting at least one of the third flip angle, the fourth flip angle, or the second characteristic parameter, and repeating (i) and (j);
wherein the second function provides a flip angle schedule corresponding to the second phase of the echo train for magnetic resonance imaging.

18. The method of claim 9, the initial condition relating to the first phase comprising at least one of an echo train duration time, an echo train length, or a phase number.

19. The method of claim 17, wherein the second function is different from the first function.

* * * * *